United States Patent [19]

Herman et al.

[11] Patent Number: 4,929,634

[45] Date of Patent: May 29, 1990

[54] METHOD OF AND BAIT COMPOSITIONS FOR CONTROLLING MOLLUSKS

[75] Inventors: Rod A. Herman, Monmouth County; Christine F. Kukel, Somerset County, both of N.J.

[73] Assignee: American Cyanamid Company, Stamford, Conn.

[21] Appl. No.: 216,097

[22] Filed: Jul. 11, 1988

Related U.S. Application Data

[63] Continuation-in-part of Ser. No. 112,904, Oct. 23, 1987, abandoned.

[51] Int. Cl.$^5$ ............................................. A01N 43/36
[52] U.S. Cl. ................................... 514/426; 514/422; 514/424; 514/427
[58] Field of Search ................ 514/422, 424, 426, 427

[56] References Cited

U.S. PATENT DOCUMENTS

| 3,428,648 | 2/1969 | Umio et al. | 260/313.1 |
| 3,963,746 | 6/1976 | Bailey | 260/326.5 |
| 4,495,358 | 1/1985 | Koyama et al. | 548/550 |
| 4,563,472 | 1/1986 | Inouye et al. | 514/381 |
| 4,705,801 | 11/1987 | Martin et al. | 514/427 |

FOREIGN PATENT DOCUMENTS

| 0206523 | 12/1986 | European Pat. Off. |
| 001528-B | 1/1969 | Japan . |
| 098562-A | 10/1985 | Japan . |

OTHER PUBLICATIONS

J. Org. Chem., 43; 4273–4276; 1978; Benages et al., p. 32, lines 14–26.

*Primary Examiner*—Allen J. Robinson
*Attorney, Agent, or Firm*—Alice C. Brennan

[57] ABSTRACT

This invention relates to methods of controlling mollusks with arylpyrrole compounds and to bait compositions containing a molluscicidally effective amount of an arylpyrrole compound.

14 Claims, No Drawings

METHOD OF AND BAIT COMPOSITIONS FOR CONTROLLING MOLLUSKS

This application is a continuation-in-part of application, Ser. No. 07/112,904, filed Oct. 23, 1987, abandoned.

BACKGROUND OF THE INVENTION

Although there is a substantial body of literature which deals with a variety of natural and synthetic pyrroles as antibacterial and antifungal agents, the use of arylpyrroles of molluscicidal agents is distinct from the art.

Fujisawa Pharmaceutical's work with the antifungal agent pyrrolnitrin (structure shown below) was disclosed in U.S. Pat. No. 3,428,648. However, the Fujisawa structures are distinct from the compounds of the present invention, and there is no reference to insecticidal activity.

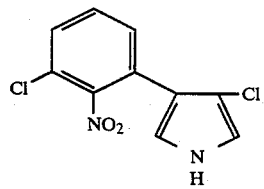

Pyrrolnitrin

Certain pyrrolomycins including antibiotic SS46506A recently isolated and identified by Meiji Seika Kaisha scientists are illustrated below. The antibiotic pyrrolomycin E contains only one pyrrole ring halogen atom. While antibiotic SS46506A is specifically claimed in U.S. Pat. No. 4,495,358, there is no mention of molluscicidal activity associated with antibiotic SS46506A either in U.S. Pat. No. 4,495,358 nor in Meiji Seika Kaisha other references on pyrrolomycins.

Meiji Seika Kaisha SS46506A and Pyrrolomycins

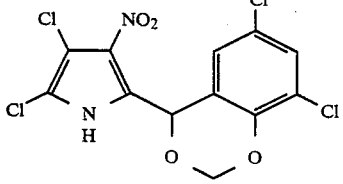

SS46506A

Pyrrolomycins

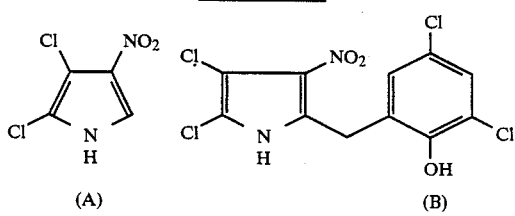

(A)  (B)

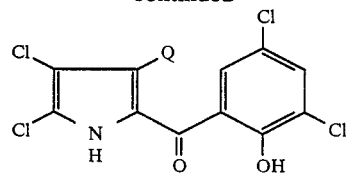

(C): Q = H
(D): Q = Cl

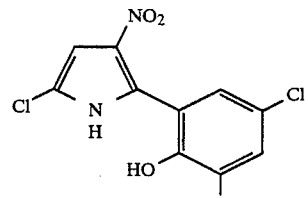

(E)

and

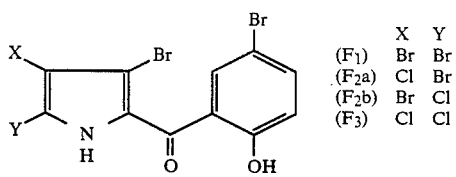

|  | X | Y |
|---|---|---|
| (F$_1$) | Br | Br |
| (F$_2$a) | Cl | Br |
| (F$_2$b) | Br | Cl |
| (F$_3$) | Cl | Cl |

Nippon Soda and Ciba Geigy have also worked in the area of pyrrole chemistry. Both gave shown that 3-aryl-4-cyano pyrroles are effective for fungicidal and bactericidal applications. Nippon Soda has disclosed 3-aryl-trihalo pyrroles as agents for the control of plant diseases.

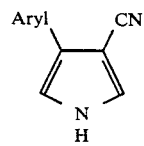

Yet another reference of interest in the pyrrole art is the U.S. Pat. No. 3,963,746 which describes 4,5-dihalopyrrol-2-yl di and tri halomethyl ketones. These compounds are said to have some activity against mites, however, the reference does not disclose or suggest any molluscicidal activity.

Other references that disclose somewhat related pyrroles include the Japanese Fujisawa Pharm. Co. ltd. patent application No. J69001528-B that describes certain aryl/cyano and aryl/nitro pyrroles wherein the pyrrole is trisubstituted and the compounds are muscle relaxants. The compounds of the present invention have a tetrasubstituted pyrrole function and the compounds are molluscicidal.

The U.S. Pat. No. 4,563,472, issued Jan. 7, 1986 and assigned to Meiji Seika Kaisha ltd. describes a number of tetrazoles that are effective as anti-microbial agents. The patentees provide a broad disclosure covering certain pyrroles, imidazoles, pyrazoles, and tetrazoles. In the case of the pyrroles, substitution may be construed to include a phenyl or a 3-chloro-2-nitrophenyl group in combination with a halogen atom and a nitro group. In all cases, the structures are substituted on nitrogen by a triiodoallyl or iodopropargyl group. There are no examples of tetra-substituted pyrroles of the types included in the present case and no finding of molluscicidal activity.

A Japanese patent application No. J62098562-A, Sanyo Electric Company on May 8, 1987 describes organic semiconductors derived from reaction products of nitrogen oxides with heterocyclic compounds. Among the broad characterization of heterocyclic compounds covered i.e. furans, thiophenes and selenophenes are included, and in a broad generic sense, certain pyrroles. However, none of the pyrroles actually described in the reference are within the disclosure of the subject application and no actual example is to be found for utilizing any pyrrole of the applicant except pyrrole itself.

European patent application No. 206523 of Imperial Chemical Industries dated Dec. 30, 1986 describes a series of fungicidal 3-alkoxy-2-heterocyclylocrylic acid esters in which the heterocylic group may encompass certain substituted pyrroles However, none of the actual examples disclosed in that case include pyrrole ring substituents which come within the scope of the generic disclosure of the subject application and, furthermore, such acrylic acid-pyrrole combinations are not a part of the molluscicidal compounds described herein.

It is therefore an object of the present invention to provide methods of and compositions for the control of mollusks and particularly to methods and compositions for controlling terrestrial gastropods such as snails, slugs and aquatic or semi-aquatic mollusks such as cowries and limpets.

These and other objects will become more apparent from the detailed description of the invention set forth below.

SUMMARY OF THE INVENTION

The present invention relates to methods of and compositions for controlling mollusks. More particularly, it relates to methods and compositions for controlling mollusks, especially terresterial gastropods, by contacting or administering to said gastropod pests a molluscicidally effective amount of an arylpyrrole compound having the structure:

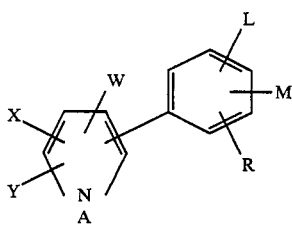

(I)

wherein X is F, Cl, Br, I, or $CF_3$; Y is F, Cl, Br, I, $CF_3$ or CN; W is CN or $NO_2$ and A is H; $C_1$–$C_4$ alkyl optionally substituted with from one to three halogen atoms, one hydroxy, one $C_1$–$C_4$ alkoxy or one $C_1$–$C_4$ alkylthio, one phenyl optionally substituted with $C_1$–$C_3$ alkyl or $C_1$–$C_3$ alkoxy or with one to three halogen atoms, one phenoxy optionally substituted with one to three halogen atoms or one benzyloxy optionally substituted with one halogen substituent; $C_1$–$C_4$ carbalkoxymethyl; $C_3$–$C_4$ alkenyl optionally substituted with from one to three halogen atoms; cyano; $C_3$–$C_4$ alkynyl optionally substituted with one halogen atom; di-($C_1$–$C_4$ alkyl) aminocarbonyl; or $C_4$–$C_6$ cycloalkylaminocarbonyl; L is H, F, Cl or Br; and M and R are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R_1CF_2Z$, $R_2CO$ or $NR_3R_4$, and when M and R are on adjacent positions and taken with the carbon atoms to which they are attached they may form a ring in which MR represents the structure:

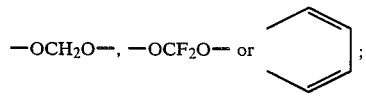

Z is $S(O)n$ or O; $R_1$ is H, F, $CHF_2$, CHFCl, or $CF_3$; $R_2$ is $C_1$–$C_3$ alkyl, $C_1$–$C_3$ alkoxy, or $NR_3R_4$; $R_3$ is H or $C_1$–$C_3$ alkyl; $R_4$ is H, $C_1$–$C_3$ alkyl, or $R_5CO$; $R_5$ is H or $C_1$–$C_3$ alkyl; and n is an integer of 0, 1 or 2. The term $C_4$–$C_6$ cycloalkylaminocarbonyl means a $C_4$–$C_6$ cycloalkylamino group attached directly to the carbonyl group through the nitrogen atom.

The present invention also provides bait compositions that contain a molluscicidally effective amount of an arylpyrrole compound having the structure illustrated above. In practice the above-said methods and compositions are especially useful for the control of terrestrial gastropods such as snails, slugs and aquatic or semi-aquatic mollusks such as cowries and limpets.

DETAILED DESCRIPTION OF THE INVENTION

A preferred group of molluscicidally effective arylpyrroles of the present invention are illustrated by formula II:

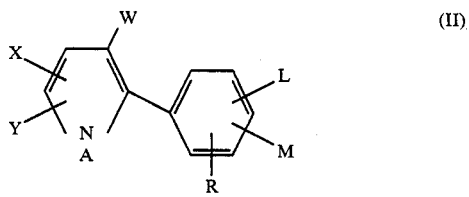

(II)

wherein A, L, M, R, W, X and Y are as described above.

Another preferred group of molluscicidal arylpyrroles of this invention are represented by formula III:

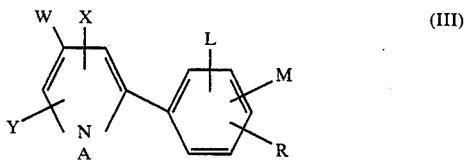

(III)

wherein A, L, R, W, X and Y are as described above.

Another group of preferred arylpyrroles of the invention which are useful for the control of mollusks are depicted by formula IV:

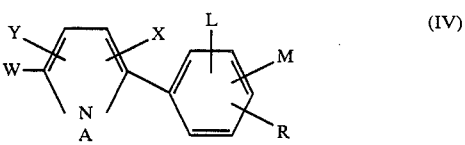

(IV)

wherein A, L, M, R, W, X and Y are as described above.

Yet another group of molluscicidal arylpyrroles of this invention are delineated by formula V:

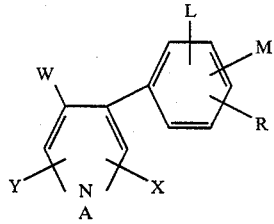

wherein A, L, M, R, W, X and Y are as described above; and still other arylpyrroles of the invention, useful as molluscicidal agents, are depicted by formulas VI and VII:

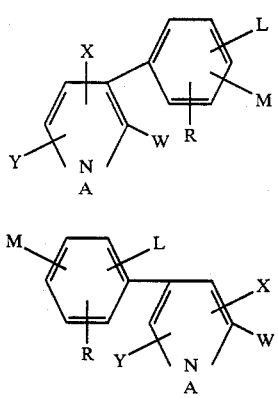

wherein A, L, M, R, W, X and Y are described above.

Preferred formula I arylpyrroles of the invention are those in which A is hydrogen, $C_1$–$C_4$ alkoxymethyl or benzyl optionally substituted with one or two $C_1$–$C_4$ alkyl, $C_1$–$C_4$ alkoxy or halogen groups; W is CN or $NO_2$; L is hydrogen, F, Cl or Br; X and Y are each F, Cl, Br or $CF_3$; M is H, F, Cl, Br, $CF_3$, $CH_3$, $OCH_3$, $OCF_3$, $OCH_2CF_3$, $SO_2CH_3$, CN, $OCF_2CHF_2$, $OCHF_2$, $SCH_3$ or $NO_2$ and R is hydrogen.

Preferred formula II compounds which are especially effective as molluscicidal agents are those wherein A is hydrogen, $C_1$–$C_4$ alkoxymethyl or benzyl optionally substituted with one or two $C_1$–$C_4$ alkyl, $C_1$–$C_4$ alkoxy or halogen groups; W is CN; X and Y are each independently F, Cl or Br; L is H, F, Cl or Br and M is H, F, Cl, Br, $CF_3$, $CH_3$, $OCH_3$, $OCF_3$, $OCH_2CF_3$, $SO_2CH_3$, CN, $OCF_2CHF_2$, $OCHF_2$, $SCH_3$ or $NO_2$ and R is hydrogen.

Other formula II compounds that are highly effective as molluscicidal agents are those in which A is hydrogen, $C_1$–$C_4$ alkoxymethyl or benzyl optionally substituted with one or two $C_1$–$C_4$ alkyl, $C_1$–$C_4$ alkoxy or halogen groups; L is hydrogen; M is hydrogen, F, Cl or Br; R is F, Cl, Br, $CF_3$ or $OCF_3$; W is $NO_2$ and X and Y are each independently Cl, Br or $CF_3$.

Illustrative of some of the most effective molluscicidal arylpyrroles of the present invention are:
4,5-dichloro-2-(3,4-dichlorophenyl)pyrrole-3-carbonitrile;
4,5-dichloro-2-[p-(trifluoromethoxy)phenyl]pyrrole-3-carbonitrile;
4-bromo-5-chloro-2-(p-chlorophenyl)pyrrole-3-carbonitrile;
5-bromo-4-chloro-2-(3,4-dichlorophenyl)pyrrole-3-carbonitrile;
4,5-dichloro-2-(o-chlorophenyl)pyrrole-3-carbonitrile;
2-(p-bromophenyl)-4,5-dichloropyrrole-3-carbonitrile;
4,5-dichloro-2-(α,α,α-trifluoro-p-tolyl)pyrrole-3-carbonitrile;
4,5-dibromo-2-(α,α,α-trifluoro-p-tolyl)pyrrole-3-carbonitrile;
4,5-dibromo-2-(o-chlorophenyl)pyrrole-3-carbonitrile;
4,5-dibromo-2-(p-chlorophenyl)pyrrole-3-carbonitrile;
4,5-dichloro-2-(2,4-dichlorophenyl)pyrrole-3-carbonitrile;
1-benzyl-4,5-dichloro-2-(3,4-dichlorophenyl)pyrrole-3-carbonitrile;
4,5-dibromo-2-(2,4-dichlorophenyl)pyrrole-3-carbonitrile;
2,3-dibromo-4-nitro-5-phenylpyrrole;
2-(p-bromophenyl)-4,5-dichloro-3-nitropyrrole;
2,3-dichloro-4-nitro-5-(α,α,α-trifluoro-p-tolyl)pyrrole;
4,5-dichloro-2-(m-chlorophenyl)pyrrole-3-carbonitrile;
4,5-dichloro-2-(p-chlorophenyl)pyrrole-3-carbonitrile;
4,5-dichloro-2-phenylpyrrole-3-carbonitrile;
2,3-dichloro-5-(p-chlorophenyl)-4-nitropyrrole;
2-bromo-3-chloro-5-(p-chlorophenyl)-4-nitropyrrole;
2,3-dibromo-5-(p-chlorophenyl-4-nitropyrrole;
2,3-dichloro-4-nitro-5-phenylpyrrole;
3-bromo-2-chloro-4-nitro-5-(α,α,α-trifluoro-p-tolyl)-pyrrole;
5-Chloro-2-(3,4-dichlorophenyl)-1-(methoxymethyl)-4-(trifluoromethyl)pyrrole-3-carbonitrile;
5-Bromo-2-(m-fluorophenyl)-3-nitro-4-(trifluoromethyl)pyrrole;
2-(p-chlorophenyl)-5-(trifluoromethyl)pyrrole-3-carbonitrile;
3-Bromo-5-(m-fluorophenyl)-4-nitro-2-(trifluoromethyl)pyrrole;
4-Bromo-2-(p-chlorophenyl)-1-(ethoxymethyl)-5-(trifluoromethyl)pyrrole-3-carbonitrile;
4-Chloro-2-(3,5-dichloro-4-methylphenyl)-3-nitro-5(trifluoromethyl)pyrrole;
2-(2-Bromo-4-chlorophenyl)-1-(2-propynyl)-4,5-bis-(trifluoromethyl)pyrrole-3-carbonitrile;
2-(2,5-Difluorophenyl)-3-nitro-4,5-bis-(trifluoromethyl)pyrrole;
5-[p-(Trifluoromethoxy)phenyl]pyrrole-2,4-dicarbonitrile;
5-(p-Dimethylaminophenyl)-4-nitropyrrole-2-carbonitrile;
3-Bromo-5-(p-chlorophenyl)pyrrole-2,4-dicarbonitrile;
4-Bromo-2-(p-chlorophenyl)-5-nitropyrrole-3-carbonitrile;
5-(p-Methylthiophenyl)-3-(trifluoromethyl)pyrrole-2,4-dicarbonitrile;
1-Allyl-4-nitro-5-(α,α,α-trifluoro-p-tolyl)-3-(trifluoromethyl)pyrrole-2-carbonitrile;
4-Chloro-2-(p-chlorophenyl)pyrrole-3-carbonitrile;
2-m-Methanesulfonylphenyl)-4-(trifluoromethyl)pyrrole-3-carbonitrile;
2-(3-chloro-4-methylphenyl)-1-methyl-3-nitro-4-(trifluoromethyl)pyrrole;
2-Phenylpyrrole-3,4-dicarbonitrile;
5-(p-Ethanesulfinylphenyl)-4-nitropyrrole-3-carbonitrile;
2-Bromo-5-phenylpyrrole-3,4-dicarbonitrile;
2-Chloro-5-(3,5-dichlorophenyl)-4-nitropyrrole-3-carbonitrile;
1-Benzyl-4-nitro-5-(p-chlorophenyl)-2-(trifluoromethyl)pyrrole-3-carbonitrile;

2-Chloro-5-(m-bromophenyl)pyrrole-3-carbonitrile;
2-Bromo-1-(p-chlorophenoxy)methyl-5-(p-chlorophenyl)-3-nitropyrrole;
2,4-Dibromo-5-phenylpyrrole-3-carbonitrile;
5-(p-Bromophenyl)-2,4-dichloro-3-nitropyrrole;
2-Bromo-5-(3-bromo-4-methylphenyl)-1-(n-propyloxy)methyl-4-(trifluoromethyl)pyrrole-3-carbonitrile;
2-Bromo-5-(p-chlorophenyl)-3-nitro-4-(trifluoromethyl)pyrrole;
5-[m-(Difluoromethoxy)phenyl]-2-(trifluoromethyl)pyrrole-3-carbonitrile;
5-(2,3-Dichlorophenyl)-1-methoxymethyl-3-nitro-2-(trifluoromethyl)pyrrole;
4-Chloro-5-(β-napthyl)-2-(trifluoromethyl)pyrrole-3-carbonitrile;
3-Bromo-2-(3,4-dichlorophenyl)-4-nitro-5-(trifluoromethyl)pyrrole;
5-(2-Bromo-5-ethylphenyl)-2,4-bis-(trifluoromethyl)pyrrole-3-carbonitrile;
1-Ethyl-2-(p-fluorophenyl)-4-nitro-3,5-bis-(trifluoromethyl)pyrrole;
1-[(2,6-Dichlorophenoxy)methyl]-5-(m-chlorophenyl)pyrrole-2,3-dicarbonitrile;
3-Nitro-5(α,α,α-trifluoro-p-tolyl)pyrrole-2-carbonitrile;
4-Chloro-5-(4-chloro-2-methylphenyl)pyrrole-2,3-dicarbonitrile;
4-Bromo-5-(3,4-dibromophenyl)-2-nitropyrrole-3-carbonitrile;
1-[(1-Methoxy)ethyl]-5-(p-chlorophenyl)-4-(trifluoromethyl)pyrrole-2,3-dicarbonitrile;
5(p-Isopropylphenyl)-2-nitro-4-(trifluoromethyl)pyrrole-3-carbonitrile;
4-Chloro-5-(3,4-difluoromethylenedioxyphenyl)pyrrole-3-carbonitrile;
3-Bromo-2-(3-chloro-4-cyanophenyl)-4-nitropyrrole;
1-[(3,4-dichlorobenzyloxy)methyl]-2-(m-bromophenyl)pyrrole-4-carbonitrile;
2-(3,5-Dichloro-4-methylphenyl)-4-nitro-3-trifluoromethylpyrrole;
2-Phenylpyrrole-3,4-dicarbonitrile;
2-(2-Bromo-4-chlorophenyl)-4-nitropyrrole-3-carbonitrile;
2-Bromo-5-phenylpyrrole-3,4-dicarbonitrile;
5-Chloro-2-(3,4-dibromophenyl)-1-methyl-4-nitropyrrole-3-carbonitrile;
2-(p-Chlorophenyl)-5-(trifluoromethyl)pyrrole-3,4-dicarbonitrile;
2-(o-Bromophenyl)-4-nitro-5-(trifluoromethyl)pyrrole-3-carbonitrile;
3-Bromo-5-(3-chloro-4-methoxy)pyrrole-2-carbonitrile;
3-Bromo-5-(m-bromophenyl)-2-nitropyrrole;
3,4-Dibromo-5-(3,4-dichlorophenyl)pyrrole-2-carbonitrile;
2-(3-Chloro-4-cyanophenyl)-5-nitro-3,4-dichloropyrrole;
3-Chloro-1-(p-methoxybenzyl)-5-(3,4-difluorophenyl)-4-trifluoromethyl)pyrrole-2-carbonitrile;
3-Bromo-5-(3,5-dibromo-p-tolyl)-2-nitro-4-(trifluoromethyl)pyrrole;
1-(2,3,3-Trichloroally)-5-(p-chlorophenyl)-3-(trifluoromethyl)pyrrole-2-carbonitrile;
2-(p-Iodophenyl)-5-nitro-4-(trifluoromethyl)pyrrole;
4-Chloro-5-(α-isopropylphenyl)-3-(trifluoromethyl)pyrrole-2-carbonitrile;
3-Bromo-1-methyl-2-(3-fluoro-4-methylphenyl)-2-nitro-3-(trifluoromethyl)pyrrole;
5-(p-Bromophenyl)-1-isopropyl-3,4-bis-(trifluoromethyl)pyrrole-2-carbonitrile;

2-(3,5-Dichloro-4-methylthiophenyl)-5-nitro-3,4-bis-(trifluoromethyl)pyrrole;
5-(m-Difluoromethoxyphenyl)pyrrole-2,3-dicarbonitrile;
5-(3-Bromo-4-cyanophenyl)-2-nitropyrrole-3-carbonitrile;
4-Chloro-1-methoxymethyl-5-(p-bromophenyl)pyrrole-2,3-dicarbonitrile;
4-Bromo-5-(2,6-dichloro-4-methylthiophenyl)-2-nitropyrrole-3-carbonitrile;
1-[(p-Bromophenoxy)methyl]-5-(m-trifluoromethylphenyl)-4-(trifluoromethyl)pyrrole-2,3-dicarbonitrile;
5-(α-Naphthyl)-2-nitro-4-(trifluoromethyl)pyrrole-3-carbonitrile;
4-Bromo-5-(3-bromo-4-trifluoromethylphenyl)pyrrole-2-carbonitrile;
3-Chloro-2-(2,3-dichlorophenyl)-5-nitropyrrole;
5-(m-Cyanophenyl)-3-(trifluoromethyl)pyrrole-2-carbonitrile;
2-(3-Bromo-4-isopropoxy)-5-nitro-3-(trifluoromethyl)pyrrole;
5-(p-Chlorophenyl)pyrrole-2,4-dicarbonitrile;
2-(3,4-Dichlorophenyl)-5-nitropyrrole-3-carbonitrile;
3-Bromo-5-(3,4-dichlorophenyl)pyrrole-2,4-dicarbonitrile;
4-Bromo-2-(3,4-dichlorophenyl)-5-nitropyrrole-3-carbonitrile;
5-(3,4-Dibromophenyl)-3-(trifluoromethyl)pyrrole-2,4-dicarbonitrile;
2-(m-Chlorophenyl)-5-nitro-4-(trifluoromethyl)pyrrole-3-carbonitrile;
5-Bromo-3-(3,5-dichloro-4-difluoromethoxyphenyl)pyrrole-2-carbonitrile;
2-Bromo-4-(2,5-dibromophenyl)-5-nitropyrrole;
2,3-Dibromo-4-(p-chlorophenyl)pyrrole-5-carbonitrile;
2,3-Dichloro-4-(3,5-difluorophenyl)-5-nitropyrrole;
5-Bromo-3-(p-chlorophenyl)-1-hydroxyethyl-4-(trifluoromethyl)pyrrole-2-carbonitrile;
2-Chloro-5-nitro-3-(trifluoromethyl)-4-(m-trifluoromethylphenyl)pyrrole;
3-(3-Bromo-4-chlorophenyl)-5-(trifluoromethyl)pyrrole-2-carbonitrile;
3-(3-Chloro-4-fluorophenyl)-2-nitro-5-(trifluoromethyl)pyrrole;
4-Bromo-3-(p-chlorophenyl)-1-methylthiomethyl-5-(trifluoromethyl)pyrrole-2-carbonitrile;
3-(4-Bromo-3-cyanophenyl)-4-chloro-2-nitro-5-(trifluoromethyl)pyrrole;
4-(p-Chlorophenyl)-2,3-bis-(trifluoromethyl)pyrrole-2-carbonitrile;
3-(2,3-Dichlorophenyl)-2-nitro-4,5-bis-(trifluoromethyl)pyrrole;
3-(3,4-Dichlorophenyl)pyrrole-2,5-dicarbonitrile;
4-(2-Bromo-4-methylphenyl)-5-nitropyrrole-2-carbonitrile;
3-Bromo-4-(3,5-dichloro-4-methylthiophenyl)pyrrole-2,5-dicarbonitrile;
4-(m-Bromophenyl)-3-chloro-5-nitropyrrole-2-carbonitrile;
3-(p-Acetamidophenyl)-4-(trifluoromethyl)pyrrole-2,5-dicarbonitrile;
4-(m-Bromophenyl)-5-nitro-3-(trifluoromethyl)pyrrole-2-carbonitrile;
4-Chloro-3-(3,4-dichlorophenyl)-1-(1-propenyl)pyrrole-2-carbonitrile;
3-Bromo-4-(p-dimethylaminophenyl)-5-nitropyrrole;

1-(3,4-Dichlorobenzyl(-3-(p-chlorophenyl)-4-(trifluoromethyl)pyrrole-2-carbonitrile;
2-Nitro-3-(p-tetrafluoroethoxyphenyl)-4-(trifluoromethyl)pyrrole;
3-(3-Bromo-4-i-propylphenyl)pyrrole-2,4-dicarbonitrile;
4-(p-Ethylsulfonylphenyl)-5-nitropyrrole-3-carbonitrile;
5-Bromo-1-(2-methoxyethyl)-3-(2,4,6-trichlorophenyl)-pyrrole-2,4-dicarbonitrile;
2-Chloro-4-(2,3-dichlorophenyl)-5-nitropyrrole-3-carbonitrile;
3-(p-Fluorophenyl)-5-(trifluoromethyl)pyrrole-2,4-dicarbonitrile;
4-(p-Iodophenyl)-5-nitro-2-(trifluoromethyl)pyrrole-3-carbonitrile;
5-Chloro-4-[p-(N-methylacetamido)phenyl]pyrrole-2-carbonitrile;
5-Bromo-4-(o-bromophenyl)-1-propargylpyrrole-2-carbonitrile;
2-Bromo-3-(o-bromophenyl)-5-nitropyrrole;
4-(p-Chlorophenyl)-3,5-dichloro-1-(2,3,3-trichloroally)-pyrrole-2-carbonitrile;
3-Bromo-5-chloro-4-(p-chlorophenyl)-2-nitropyrrole;
5-Bromo-4-[p-(2,2-dichloro-1,1-difluoroethoxy)-phenyl]-3-(trifluoromethyl)pyrrole-2-carbonitrile;
2-Chloro-3-(2-bromo-4-ethylthiophenyl)-5-nitro-4-(trifluoromethyl)pyrrole;
3-(3-Bromo-4-acetylphenyl)-5-(trifluoromethyl)pyrrole-2-carbonitrile;
1-Cyano-3-(3,4-dibromophenyl)-5-nitro-2-(trifluoromethyl)pyrrole;
3-Bromo-1-methoxymethyl-4-(m-trifluoromethyl)-5-(trifluoromethyl)pyrrole-2-carbonitrile;
3-(p-Chlorophenyl)-4-iodo-5-nitro-2-(trifluoromethyl)-pyrrole;
4-(p-Bromophenyl)-1-[(1-ethoxy)ethyl]-3,5-di-(trifluoromethyl)pyrrole-2-carbonitrile;
3-(2-Bromo-4-methoxyphenyl)-5-nitro-2,4-di-(trifluoromethyl)pyrrole;
3-(p-Chlorodifluoromethoxyphenyl)pyrrole-2,5-dicarbonitrile;
2-(p-Isobutyrylaminophenyl)-5-nitropyrrole-2-carbonitrile;
3-Bromo-4-(3,4-dimethoxyphenyl)pyrrole-2,5-dicarbonitrile;
4-Chloro-3-(p-chlorophenyl)-1-isopropyloxycarbonylmethyl)-5-nitropyrrole-2-carbonitrile;
3-o-Bromophenyl)4-(trifluoromethyl)pyrrole-2,5-dicarbonitrile;
1-(2-Chloroethyl)-3-(3,4-dichlorophenyl)-4-(trifluoromethyl)pyrrole-2-carbonitrile;
4-(4-Bromo-3-trifluoromethoxyphenyl)-3-chloropyrrole-2-carbonitrile;
3-Bromo-4-(2,4-dichlorophenyl)-1-isopropyl-2-nitropyrrole;
4-(3-Methoxy-4-cyanophenyl)-3-(trifluoromethyl)pyrrole-2-carbonitrile;
1-(3,4-Dichlorobenzyl)-4-(2-methyl-4-iodophenyl)-2-nitro-3-trifluoromethylpyrrole;
1-Methyl-4-[3,5-di(trifluoromethyl)phenyl]pyrrole-2,3-dicarbonitrile;
4-(3,4-Dichlorophenyl)-2-nitropyrrole-3-carbonitrile;
4-Bromophenyl)-1-carbomethoxymethyl-5-chloropyrrole-2,3-dicarbonitrile;
5-Bromo-4-(2,6-dichloro-4-methanesulfinylphenyl-2-nitropyrrole-3-carbonitrile;
4-Chlorophenyl)-1-(2,2,2-trifluoroethyl)-5-(trifluoromethyl)pyrrole-2,3-dicarbonitrile;
4-(3,5-Dichlorophenyl)-2-nitro-5-(trifluoromethyl)pyrrole-3-carbonitrile;
2-Chloro-4-(3-chloro-4-N-methylacetamidophenyl)pyrrole-3-carbonitrile;
2-Bromo-4-(3-bromo-4-D-propylphenyl)-3-nitropyrrole;
2,5-Dichloro-4-(3,5-dichloro-4-methylthiophenyl)pyrrole-3-carbonitrile;
2,5-Dibromo-1-(2,4-dibromophenoxymethyl)-3-(p-chlorophenyl-4-nitrpyrrole;
4-(3-Bromo-4-cyanophenyl)-2-chloro-5-(trifluoromethyl)pyrrole-3-carbonitrile;
2-Bromo-1-methyl-3-nitro-4-($\alpha,\alpha,\alpha$-trifluoro-p-tolyl)-pyrrole;
4-(p-chlorophenyl)-1-(n-butyloxymethyl)-5-(trifluoromethyl)pyrrole-3-carbonitrile;
4-(3,4-Methylenedioxyphenyl)-3-nitro-2-(trifluoromethyl)pyrrole;
5-Chloro-4-(3-chloro-4-trifluoromethoxyphenyl)-2-(trifluoromethyl)pyrrole-3-carbonitrile;
2-Bromo-3-(3,4-dichlorophenyl)-1-ethylthiomethyl-4-nitro-5-(trifluoromethyl)pyrrole;
4-[p-(tetrafluoroethoxy)phenyl]-2,5-di-(trifluoro methyl)pyrrole-3-carbonitrile;
3-(3-Bromo-4-acetoxyphenyl)-1-(3,4-dichlorophenoxymethyl)-4-nitro-2,5-di-)trifluoromethyl)pyrrole;
4-(p-Bromophenyl)-1-[(2-methoxy)ethyl]pyrrole-2,3-dicarbonitrile;
4-Isopropionamidophenyl)-3-nitropyrrole-2-carbonitrile;
5-Bromo-4-(2-chloro-4-methylthiophenyl)pyrrole-2,3-dicarbonitrile;
5-Chloro-4-(p-chlorophenyl)-1-hydroxyethyl-3-nitropyrrole-2-carbonitrile;
4-(3,5-Dibromo-4-cyanophenyl)-5-(trifluoromethyl)-pyrrole-2,3-dicarbonitrile;
4-(4-Chloro-2-methylphenyl)-1-isopropylthiomethyl-3-nitro-5-(trifluoromethyl)pyrrole-2-carbonitrile;
5-Bromo-4-(3,4-dichlorophenyl)-1-(difluoromethyl)-pyrrole-3-carbonitrile;
2-Chloro-3-(m-difluoromethoxyphenyl)-4-nitropyrrole;
1-(2,4-Dibromophenoxymethyl)-4-(m-chlorophenyl)-5-(trifluoromethyl)pyrrole-3-carbonitrile;
3-(3-Bromo-4-ethoxyphenyl)-4-nitro-2-(trifluoromethyl)pyrrole;
3-(2,4,6-Trichlorophenyl)pyrrole-2,4-dicarbonitrile;
3-(4-Bromo-3-chlorophenyl)-!-(difluoromethyl)-4-nitropyrrole-2-carbonitrile;
5-Bromo-3-(p-chlorophenyl)-1-(isobutyloxymethyl)-pyrrole-3-carbonitrile;
3-(4-Bromo-3-methylphenyl)-5-chloro-4-nitropyrrole-2-carbonitrile;
3-(2-Naphthyl)-5-(trifluoromethyl)pyrrole-2,4-dicarbonitrile;
3-(3-Cyano-4-methylphenyl)-1-methyl-4-nitro-5-(trifluoromethyl)pyrrole-2-carbonitrile;
2,3-dichloro-5-(3,4-dichlorophenyl)-4-nitropyrrole;
2-(3,5-dibromo-4-methoxyphenyl)-4,5-dichloropyrrole-3-carbonitrile;
2,3-dichloro-4-nitro-5-(2,4,6-trifluorophenyl)pyrrole;
4,5-dibromo-2-(2,3,6-trifluorophenyl)-3-carbonitrile;
4,5-dichloro-2-(3,4-dichlorophenyl)-1-(ethoxymethyl)-pyrrole-3-carbonitrile;
4,5-dibromo-1-methyl-2-($\alpha,\alpha,\alpha$-trifluoro-p-tolyl)pyrrole-3-carbonitrile;

4,5-dichloro-2-(3,4-dichlorophenyl)-1-ethylpyrrole-3-carbonitrile;
2,3-dichloro-4-nitro-5-[p-(trifluoromethoxy)phenyl]-pyrrole;
4,5-dichloro-2-[m-(trifluoromethoxy)phenyl]pyrrole-3-carbonitrile;
4,5-dichloro-2-(3,4-dichlorophenyl)-1-methylpyrrole-3-carbonitrile;
2,3-dichloro-5-(p-chlorophenyl)-1-methyl-4-nitropyrrole; and
4-bromo-5-chloro-2-(p-chlorophenyl)-1-methylpyrrole-3-carbonitrile;
5-chloro-2-(3,4-dichlorophenyl)-4-fluoropyrrole-3-carbonitrile;
2-bromo-5-(p-chlorophenyl)-1-(ethoxymethyl)-4-fluoropyrrole-3-carbonitrile;
3-bromo-5-(p-chlorophenyl)-2-fluoro-4-nitropyrrole.

The molluscicidal arylpyrrole compounds of formula I, wherein A is hydrogen; W is CN and L, M and R are as described above, can be prepared by reacting N-formyl-DL-phenyl-glycine or a substituted N-formyl-phenylglycine represented by the structure formula VIII:

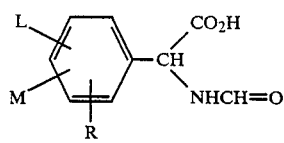
(VIII)

wherein L is H, F, Cl or Br; R and M are each independently H, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, cyano, F, Cl, Br, I, nitro, $CF_3$, $R_1CF_2Z$, $R_2CO$ or $NR_3R_4$ and when on adjacent positions and taken together with the carbon atoms to which they are attached, M and R may form a ring in which MR represents the structure:

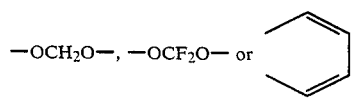

Z is $S(O)n$ or O; $R_1$ is H, F, $CHF_2$, CHFCl or $CF_3$; $R_2$ is $C_1$-$C_3$ alkyl, $C_1$-$C_3$ alkoxy or $NR_3Rhd\ 4$; $R_3$ is H or $C_1$-$C_3$ alkyl; $R_4$ is H, $C_1$-$C_3$ alkyl or $R_5CO$; $R_5$ is H or $C_1$-$C_3$ alkyl and n is an integer of 0, 1 or 2; with at least an equivalent amount of a 2-chloroacrylonitrile and two to three equivalents of acetic anhydride. The reaction is conducted at an elevated temperature, preferably about 70° to 100° C.

The reaction can be illustrated as follows:

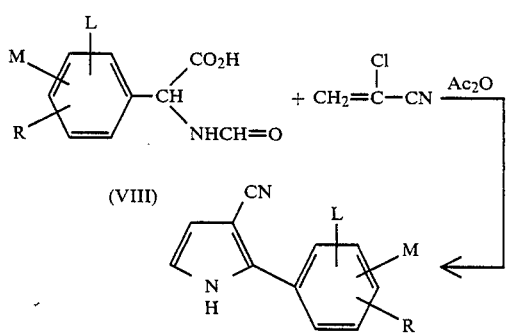

Conversion of the thus prepared 2-phenylpyrrole-3-carbonitrile or 2-(substituted phenyl)pyrrole-3-carbonitrile to the corresponding formula II, 4-halo, 5-halo or 4,5-dihalo-2-(substituted phenyl)pyrrole-3-carbonitrile, is readily achieved by reaction of the above said 2-phenylpyrrole-3-carbonitrile or 2-(substituted phenyl)-pyrrole-3-carbonitrile with at least about 1 or 2 equivalents of a sulfuryl halide, bromine or chlorine, in the presence of a solvent such as dioxane, THF, acetic acid or a chlorinated hydrocarbon solvent. For preparation of a monohalo pyrrole-3-carbonitrile use of about 1 equivalent of the halogenating agent is required; whereas, preparation of a dihalo or trihalo pyrrole-3-carbonitrile requires 2 to 3 equivalents of said halogenating agent. When sulfuryl chloride or sulfuryl bromide is used the reaction is generally conducted at a temperature below about 40° C. and preferably between about 0° and 30° C., but when elemental bromine is employed, the reaction is usually conducted at about 30°-40° C. Other effective halogenating agents that may be employed in these reactions include sodium hypochlorite, t-butylhypochlorite, N-bromosuccinimide, and the like. The reaction may be illustrated as follows:

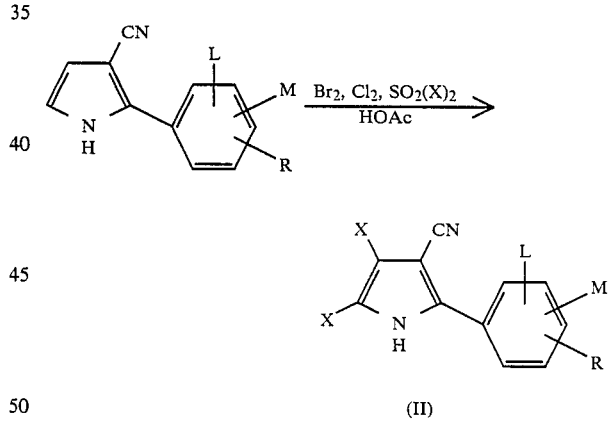

(II)

The formula II carbonitrile compounds of the present invention may also be prepared from the reaction of a substituted or unsubstituted benzoyl acetonitrile with a 2,2-di($C_1$-$C_4$ alkoxy)ethylamine in the presence of an aromatic solvent to form the ($C_1$-$C_4$ alkoxy)ethylamino)-β-cyano-(substituted)styrene which is then converted to the 2-(substituted-phenyl)pyrrole-3-carbonitrile of formula II by reaction of said β-3-cyano-(substituted)styrene compound with trifluoroacetic acid or with concentrated HCl temperature between about 20° and 40° C. The reaction may be graphically illustrated as follows:

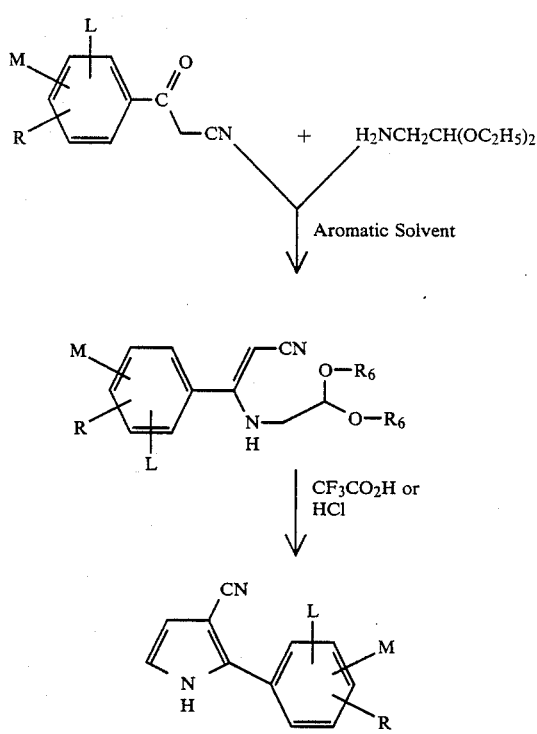

wherein $R_6$ is $C_1$–$C_4$ alkyl and L, R and M are as described above.

Also in accordance with the present invention formula II 3-nitro-2-phenylpyrrole and 3-nitro-2-(substituted)phenylpyrrole compounds can be prepared by reaction of an α-nitroacetophenone or a substituted α-nitroacetophenone with a 2,2-di($C_1$–$C_4$-alkoxy)ethylamine. The reaction is generally conducted in the presence of an inert organic solvent preferably an aromatic solvent, at an elevated temperature to give an α-(2,2-di($C_1$–$C_4$- alkoxy)ethylamino)-β-nitrostyrene or a substituted α-(2,2-di($C_1$–$C_4$-alkoxy)ethylamino)-β-nitrostyrene that is converted to the formula II 3-nitro-2-phenylpyrrole or 3-nitro-2-(substituted)phenylpyrrole by treatment with a mineral acid such as hydrochloric or hydrobromic acid. Reaction of the thus prepared nitrophenylpyrrole with sodium hypochlorite in the presence of an inert organic solvent at a reduced temperature yields the formula II 2,3-dichloro-4-nitro-5-phenyl or 5-(substituted)phenylpyrrole.

The above reactions may be graphically illustrated as follows:

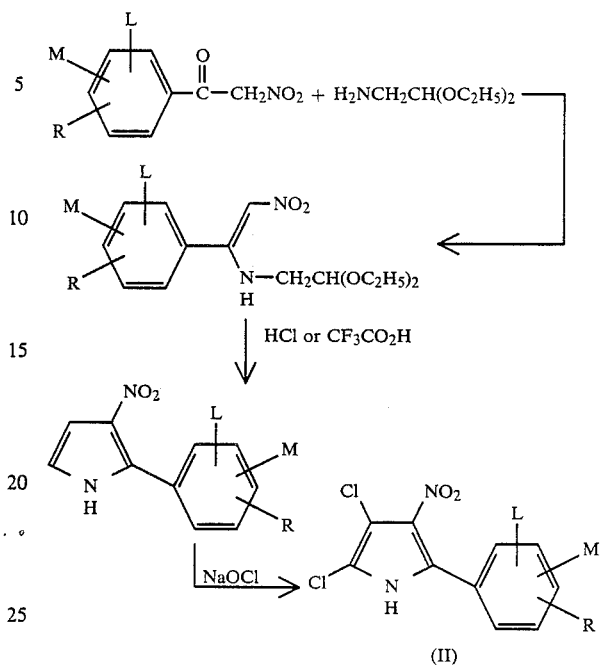

In addition to the several methods described in the literature for preparing substituted and unsubstituted benzoyl acetonitriles, surprisingly we have found that these compounds may also be prepared by reacting an appropriately substituted benzoyl halide with an alkali metal hydride and an alkyl cyanoacetate, such as t-butyl cyanoacetate, to yield the corresponding t-butyl(benzoyl or substituted benzoyl)cyanoacetate. These reactions may be graphically illustrated as follows:

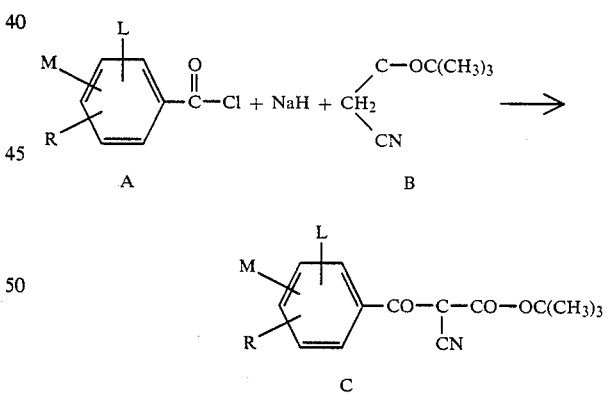

The thus formed cyanoacetate ester can then be converted to a substituted or unsubstituted benzoyl acetonitrile by heating the compound in toluene containing p-toluene sulfonic acid. The reaction may be graphically illustrated as follows:

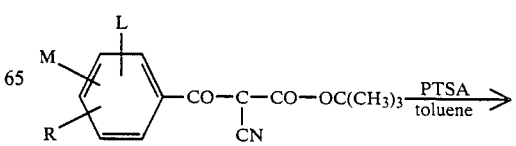

-continued

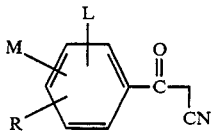

Examples of the t-butyl(benzyl and substituted benzoyl acetonitriles used in the above reactions are shown in Tables below.

| L | M | R | mp °C. |
|---|---|---|---| t-Butyl(benzoyl and Substituted benzoyl)cyanoacetates (structure: Ar—CO—C(CN)—CO—OC(CH$_3$)$_3$)

| L | M | R | mp °C. |
|---|---|---|---|
| H | 3-Cl | 4-Cl | 91–94 |
| H | H | 4-OCF$_3$ | 81–84 |
| H | H | 4-Br | 113–115 |
| H | H | 4-CF$_3$ | 146–147 |
| H | H | 4-F | 98–100 |
| H | H | 4-CN | 127–128 |
| H | H | 4-CF$_3$CH$_2$O | 136–139 |
| H | H | 4-CH$_3$SO$_2$ | 127–129 |
| H | 3-F | 4-F | 91–94 |
| H | H | 4-CH$_3$S | 117–119.5 |
| H | H | 4-CHF$_2$CF$_2$O | 92–94 |
| 3-Cl | 5-Cl | 4-CH$_3$O | — |

Benzoyl Acetonitriles (structure: Ar—CO—CH$_2$CN)

| L | M | R | mp °C. |
|---|---|---|---|
| H | H | 4-Cl | 128.5–129.5 |
| H | 3-Cl | 4-Cl | 105–107 |
| H | H | 2-C | 153–55 |
| H | H | 4-OCF$_3$ | 79–81 |
| H | H | 4-CF$_3$ | 44–45 |
| H | 2-Cl | 4-Cl | 66–67 |
| H | H | 3-Cl | 80–83 |
| H | H | 4-CN | 126–128 |
| H | H | 4-F | 78–80 |
| H | H | 4-SO$_2$CH$_3$ | 129–132 |
| H | 3-F | 4-F | 74–75 |
| H | H | 3-CF$_3$ | 58–60 |
| H | H | 4-CH$_3$ | 103.5–106 |
| H | H | 4-NO$_2$ | 119–124 |
| 3-Cl | 5-Cl | 4-OCH$_3$ | — |

Preparation of N-substituted formula I arylpyrroles can be achieved by reaction of the appropriately substituted formula I arylpyrrole, wherein A is hydrogen and L, M, R, W, X and Y are as described above, with a brominated hydroxy-C$_1$–C$_4$-alkyl and potassium t-butoxide. This reaction provides an arylpyrrole having the same substituents as the starting material, but in addition is substituted on the nitrogen with hydroxy-C$_1$–C$_4$ alkyl. In a similar reaction cyanogen bromide is substituted for the brominated hydroxy C$_1$–C$_4$ alkyl and yields the formula I arylpyrrole with a carbonitrile substituent on the nitrogen. The reaction may be illustrated as follows:

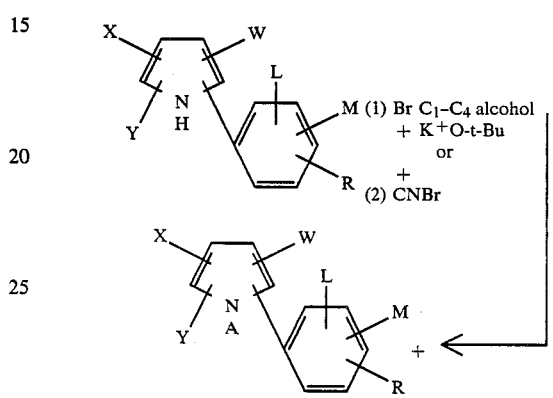

wherein L, M, R, W, X and Y are as described for formula I above and a is (1) C$_1$–C$_4$ alcohol or (2) CN.

Preparation of 2-phenylpyrrole 3,4-dicarbonitrile, 2-bromo-5-phenylpyrrole-3,4-dicarbonitrile and substituted phenyl derivatives thereof can be obtained by reaction of fumaronitrile with bromine in the presence of a chlorinated hydrocarbon such as chloroform at an elevated temperature to yield bromofumaronitrile. The thus formed bromofumaronitrile is then reacted with N-(trimethylsilyl)methyl-5-methyl-benzene-thioimidate or a substituted derivative thereof, in the presence of hexamethylphosphoramide at an elevated temperature to yield the 2-phenylpyrrole-3,4-dicarbonitrile of the substituted 2-phenylpyrrole-3,4-dicarbonitrile. Bromination of the thus prepared 3,4-dicarbonitrile yields the 2-bromo-5-phenylpyrrole-3,4-dicarbonitrile or the substituted phenyl derivative if the substituted N-(trimethylsilyl)methyl-5-methyl-benzene-thioimidate is used in the previous reaction. The reaction may be graphically illustrated as follows:

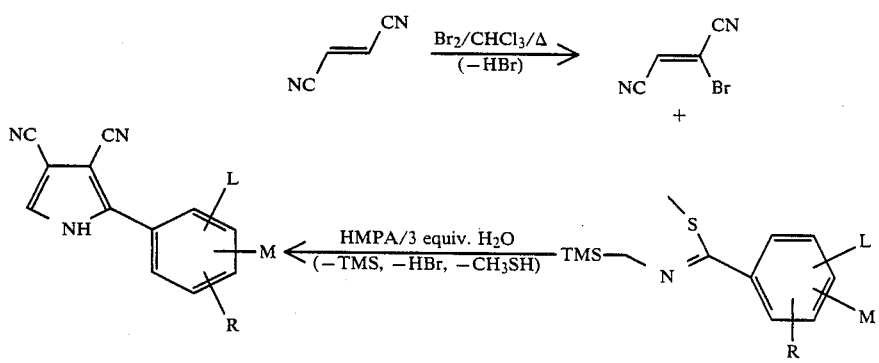

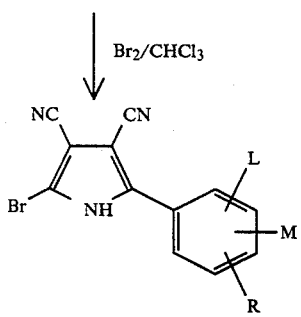

The arylpyrroles of the present invention are effective for controlling mollusks particularly terresterial gastropods. These compounds are also effective for protecting growing or harvested crops from attack by the above-said pests.

In practice generally about 10 ppm to about 10,000 ppm and preferably 100 to about 5000 ppm, of the molluscidial arylpyrrole dispersed in water or other water miscible solvent is effective when introduced into ponds, lakes, irrigation canals and the like to inhibit the development of snails and other mollusks and/or eliminate said creatures from said lakes, ponds, canals, irrigation systems and the like.

The arylpyrroles of this invention are also effective for controlling terresterial gastropods, when applied to the foliage of plants and/or to the soil in which said plants are growing. These applications are usually in the form of dusts or dust concentrates and are usually applied in sufficient amount to provide a rate of from about 0.125 kg/ha to about 4.0 kg/ha of active ingredient.

For the protection of growing plants it is also found that said plants may be sprayed with an aqueous or liquid spray containing from about 10 ppm to 10,000 ppm and preferably 100 to 5000 ppm of the formula I arylpyrrole, and generally such application should provide about 0.125 kg/ha to 4.0 kg/ha of the active ingredient to the locus of the plants being sprayed.

The arylpyrroles of the present invention are also very effective for controlling terresterial gastropods by proffering the active material in bait formulations. These baits generally contain about 3% to 20% by weight and preferably about 5% to 10% by weight of the active ingredient, about 40% to 50% by weight of a solid edible nutritive substance, about 5% to 10% by weight of a carbohydrate source such as sugar, molasses, corn syrup or the like and the remainder of the formulation, i.e. about 30% to 50% by weight of water or other consumable liquid.

A preferred bait formulation will contain about 5% by weight of the arylpyrrole dispersed in a bait comprising about 46% of unprocessed bran, 6% by weight of molasses and 48% by weight of water.

Advantageously, the above-said arylpyrroles may also be formulated as flowable compositions, wettable powders, microemulsions and the like, all of which lend themselves to soil, water and/or foliage application and provide the requisite plant protection. Such formulations include the compounds of the invention admixed with inert, pharmacologically-acceptable solid or liquid diluents.

For example, wettable powders, dusts and dust concentrate formulations of the invention can be prepared by grinding together about 3% to 20%, by weight, of the formula I arylpyrrole compound, with about 3% to 20% by weight of a solid anionic surfactant. One suitable anionic surfactant is a dioctyl ester of sodium sulfosuccinic acid, specifically Aerosol OTB ® surfactant marketed by the American Cyanamid Company. About 60% to 94%, by weight, of an inert solid diluent, such as montmorillonite, attapulgite, chalk, talc, kaolin, diatomaceous earth, limestone, silicates or the like is also included in such formulations.

In addition to the dusts, dust concentrates and wettable powder formulations described hereinabove, flowable formulations may be used since they are readily dispersible in water and may be applied to the breeding grounds, food supply or habitat of the mollusks sought to be controlled.

The following examples are presented as illustrations of the present invention.

EXAMPLE 1

2-Phenylpyrrole-3-carbonitrile

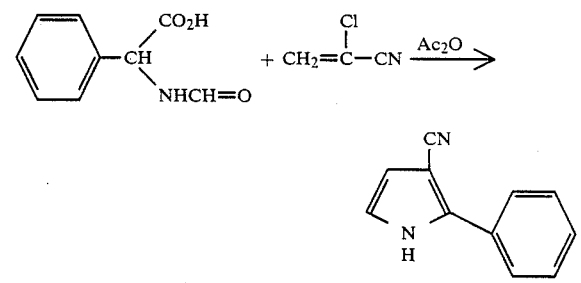

The following procedure is similar to the method given in JOC, 43, 4273–6 (1978). A magnetically stirred mixture of 30.00 g of N-formyl-phenylglycine is heated at 90° C. for 1½ hours. The clear yellow reaction solution is concentrated in vacuo to give 42.5 g of an oily brownish orange semi-solid. Material partially purified by chromatography on silica gel is shown by the proton NMR spectrum to be a mixture of 73% 2-phenylpyrrole-3-carbonitrile and 27% 2-phenyl-3-cyano-5-methylpyrrole. Recrystallization once from chloroform and twice from 1,2-dichloroethane gives 1.69 g of an off-white solid which proton NMR shows it to be 96% 2-phenylpyrrole-3-carbonitrile, mp 148°–152° C.

Microanalysis (MW 168.19): Calcd.: C, 78.55%; H, 4.79%; N, 16.66%. Found: C, 78.52%; H, 4.73%; N, 16.54%.

EXAMPLE 2

4,5-Dichloro-2-phenylpyrrole-3-carbonitrile and 5-chloro-2-phenylpyrrole-3-carbonitrile

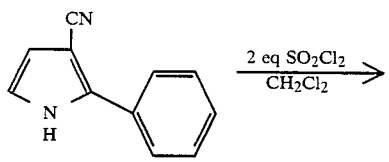

To a magnetically stirred ice-water cooled solution of 200 g (11.9 mmol,) of 2-phenyl-3-cyanopyrrole in 80 mL of methylene chloride is added dropwise over a period of 5 min., 1.90 mL (3.19 g, 23.6 mmol,) of sulfuryl chloride by means of a syringe. Throughout the addition the temperature is kept between 5° C. and 10° C. Stirring at 5°–10° C. is continued for 90 minutes. The reaction mixture is vacuum filtered to remove a precipitated solid (1.28 g) identified as 5-chloro-2-phenylpyrrole-3-carbonitrile, mp 192.5°–195° C. The filtrate is diluted with 400 ML of ethyl acetate, washed twice with 200 mL of water, dried (sodium sulfate), treated with charcoal, filtered. and then concentrated in vacuo to give (after slurrying of the residue with hexane) 0.06 g (21.3% yield) of a pink-purple solid. This solid is recrystallized from 5 mL of hot acetone to give 0.32 g (9% yield) of 4,5-dicloro-2-phenylpyrrole-3-carbonitrile as an organish brown solid, mp 254°–255° C.

EXAMPLE 3 p-Chloro-β-[(formylmethyl)amino]cinnamonitrile, diethyl acetal

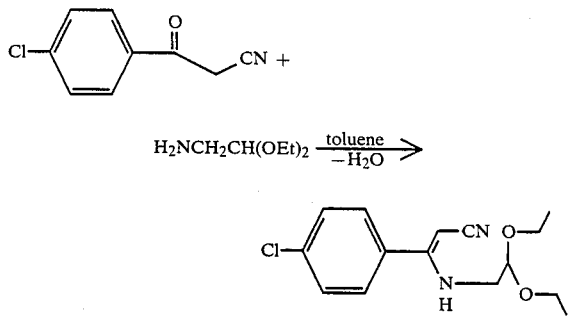

A magnetically stirred solution of 250.00 g (1.39 mol,) of p-chlorobenzoylacetonitrile, 203 mL (185.95 g, 1.39 mol) of 2,2-diethoxyethylamine, and 1300 mL of dried toluene is heated at reflux for 20 hours. Water is collected in a Dean-Stark trap (23.8 mL, 95.2% theory). The hot cloudy dark brown solution with a large amount of undissolved solids is filtered through diatomaceous filter aid. After dilution with 200 mL of EtOAc, the solution is filtered through a 7 cm × 13.5 cm column of silica gel. The filtrate is concentrated in vacuo to give 354.38 g (86.4% crude yield) of a clear dark oil which slowly solidifies. This solid is recrystallized from hot cyclohexane to give 324.26 g (79.1% yield) of a waxy orange solid. NMR of this product shows it to be composed of 78% (Z) and 23% (E) isomeric mixture of p-chloro-β-[(formylmethyl)amino]cinnamonitrile, diethyl acetal, m.p. 60°–72° C. The following analytical data is for another similarly prepared sample.

EXAMPLE 4

2(p-Chlorophenyl)-pyrrole-3-carbonitrile

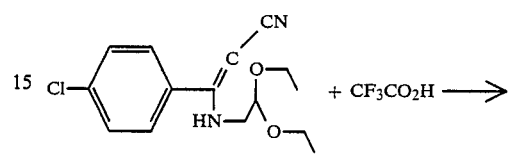

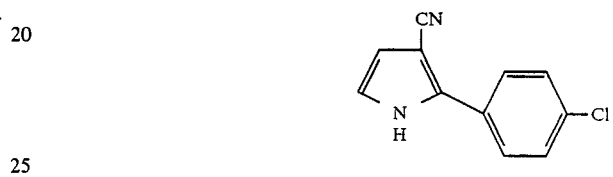

To 108 mL of trifluoroacetic acid stirred at 23° C. is added 54.00 g (0.183 mol) of solid p-chloro-β-[(formylmethyl)amino]cinnamonitrile, diethyl acetal over a period of 45 minutes. This addition produced an exotherm to 38° C. and, 32 minutes into the addition, a solid started to precipitate. After stirring at room temperature for 30 minutes, the reaction mixture is vacuum filtered and the collected solid is washed first with trifluoroacetic acid, secondly with an ethyl acetate-hexane mixture, and finally with hexane. The yield is 16.83 g (45.4%) of an off-white solid, mp 165°–166° C. The following anal. data is from a similarly prepared sample.

Use of the above procedure as shown or with the substitution of concentrated hydrochloric acid for trifluoroacetic acid affords the following compounds:

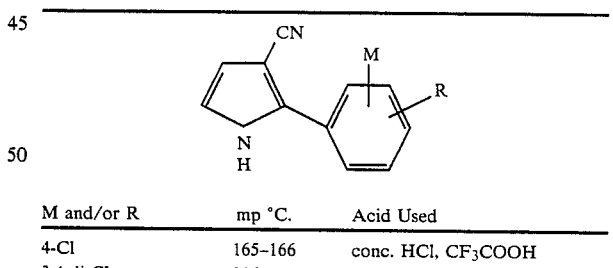

| M and/or R | mp °C. | Acid Used |
|---|---|---|
| 4-Cl | 165–166 | conc. HCl, CF₃COOH |
| 3,4-di-Cl | 216–221 | CF₃COOH |
| 2-Cl | 156–157 | CF₃COOH |
| 4-OCF₃ | 143–145 | CF₃COOH |
| 4-CF₃ | 179–180 | CF₃COOH |
| 2,4-di-Cl | 197–199 | CF₃COOH |
| 3-Cl | 150–156 | CF₃COOH |
| 4-CN | 210–212 | CF₃COOH |
| 4-F | 167–170 | conc. HCl |
| 4-SO₂CH₃ | 221–221.5 | CF₃COOH |
| 3,4-di-F | 173–175.5 | CF₃COOH |
| 3-CF₃ | 166–168 | CF₃COOH |
| 4-COOCH₃ | 155.5–158 | CF₃COOH |
| 4-CH₃ | 117–137 | CF₃COOH |
| 4-NO₂ | 174–177 | CF₃COOH |

EXAMPLE 5

4,5-Dichloro-2-(p-chlorophenyl)pyrrole-3-carbonitrile

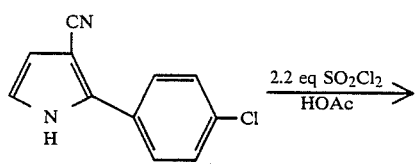

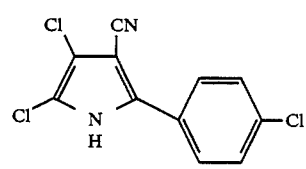

To a mechanically stirred solution of 16.83 g (83.1 mmol) of 2-(p-chlorophenyl)pyrrole-3-carbonitrile in 450 mL of glacial acid at 36° C. is added dropwise 14.7 mL (24.70 g, 183.0 mmol) of sulfuryl chloride over a period of 18 minutes. The addition produces a slight exotherm to 39° C. and, after another 16 minutes, the reaction mixture is vacuum filtered. The collected solids are washed first with acetic acid and then with water. This solid after recrystallization from hot ethyl acetate, melts at 259°–261° C.

EXAMPLE 6

4,5-Dibromo-2-(α,α,α-trifluoro-p-tolyl)-pyrrole-3-carbonitrile

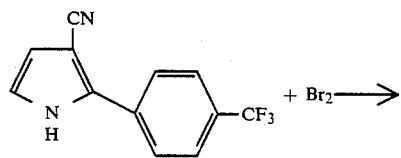

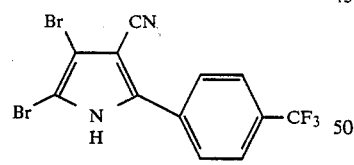

To a stirred mixture of 0.8 g of 2-(α,α,α-trifluoro-p-tolyl)pyrrole-3-carbonitrile in 70 mL of chloroform is added 2 mL of bromine. The mixture, on stirring overnight, deposits a white solid which is collected by filtration. Thin layer chromatography (1:1 ethyl acetate-hexane) shows a single component; m.p. >230° C.

Anal. Calc'd for $C_{12}H_5Br_2F_3N_2$; C, 36.55; H, 1.27; N, 7.11; Br, 40.61. Found: C, 36.40; H, 1.08; N, 6.99; Br, 40.55.

Following the above procedure but substituting the appropriately substituted phenylpyrrole-3-carbonitrile for 2-(α,α,α-trifluoro-p-tolyl)pyrrole-3-carbonitrile yields the following compounds.

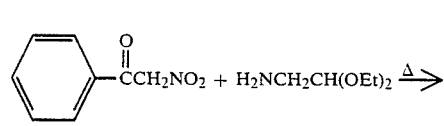

| L | M | R | X | Y | mp °C. |
|---|---|---|---|---|---|
| H | H | 4-NO$_2$ | Br | Br | 274–277 |
| H | H | 4-F | Cl | Cl | >220 |
| H | H | 4-F | Br | Br | >220 |
| H | H | 4-SO$_2$CH$_3$ | Cl | Cl | >230 |
| H | 3-F | 4-F | Cl | Cl | >230 |
| H | 3-F | 4-F | Br | Br | >220 |
| 2-Cl | 3-Cl | 4-Cl | Cl | Cl | |
| 2-Br | 3-Br | 4-Br | Br | Br | |
| H | H | 4-OCF$_3$ | Cl | Cl | 222–225 |
| H | H | 4-OCF$_3$ | Br | Br | 231–232 |
| H | H | 4-OCF$_3$ | Cl | H | |
| H | H | 4-CN | Br | Br | >230 |
| H | H | 4-CN | Cl | Cl | >240 |
| H | H | 4-SO$_2$CH$_3$ | Br | Br | >230 |
| H | H | 4-NO$_2$ | Cl | Cl | 246–249 |
| H | 3-Cl | 4-Cl | Br | Br | >260 |
| H | H | 3-CF$_3$ | Cl | Cl | >230 |
| H | H | 4-COCH$_3$ | Cl | Cl | 251–254 |
| H | 2,3-CH=CH— | | Cl | Cl | 244–247 |
| H | H | 4-CH$_3$ | Cl | Cl | 215–217 |
| H | 2-Cl | 4-Cl | Br | Br | >230 |
| H | H | 3-Cl | Cl | Cl | >230 |
| H | 2-Cl | 4-Cl | Cl | Cl | >230 |
| H | H | 4-Cl | Br | Br | 273–274 |
| H | H | 2-Cl | Br | Br | >230 |
| H | H | 4-CF$_3$ | Cl | Cl | >230 |
| H | H | 4-Br | Cl | Cl | >235 |
| H | H | 2-Cl | Cl | Cl | >230 |
| H | 3-Cl | 4-Cl | Cl | Cl | >235 |
| H | H | H | Cl | Cl | 254–255 |
| H | H | 4-Cl | Cl | Cl | 255–257 |
| H | H | 4-CF$_3$ | Br | Br | >230 |
| H | H | 4-Cl | Cl | Br | 262–263 (dec.) |
| H | H | 4-Cl | Br | Cl | 250–258 (dec.) |
| H | 3-Cl | 5-Cl | Cl | Cl | >230 |
| H | 3-Cl | 4-Cl | Cl | Br | >230 |
| 2-Cl | 4-Cl | 5-F | Cl | Cl | 207–210 |

EXAMPLE 7

3-Nitro-2-phenylpyrrole

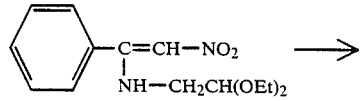

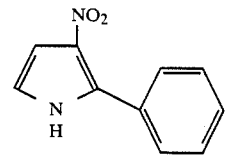

Alpha-nitro acetophenone (5.7 g, 0.0345 mol) is taken up in 100 mL toluene and 4.6 g (0.0345 mol) of amino acetaldehyde diethyl acetal is added. The reactants are put into a 250 mL RB flask fitted with a Dean-Stark trap. The trap is filled with 4A molecular sieves and the mixture is heated at reflux for 18 hours. The toluene is removed in vacuo to give 8.36 g of α-(2,2-diethoxyethylamino)-β-nitrostyrene as a brown oil. To this oil is added 50 mL of concentrated HCl. As the flask is swirled the oil turns to a yellow suspension. After 10 minutes the solid is filtered to give 2.48 g of a yellow solid. Recrystallization from ether/ethylacetate/hexane gives the product as two fractions, 2.08 g of m.p. 190°-192° C., (31%).

EXAMPLE 8

2,3-Dichloro-4-nitro-5-phenylpyrrole

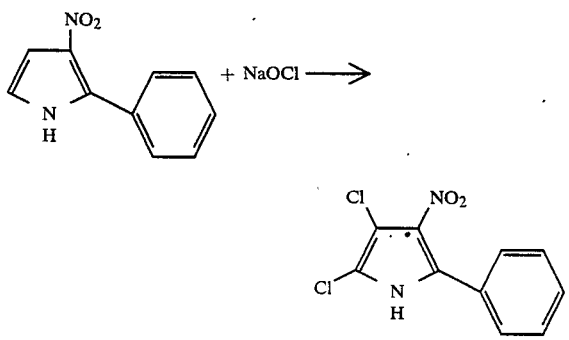

A mixture of 3-nitro-2-phenylpyrrole (1.56 g, 0.0083 mol) in 60 mL of dioxane is cooled in an ice bath while 25.9 g (0.0182 mol) of commercial sodium hypochlorite is added dropwise. After stirring for 45 minutes, the mixture is acidified with concentrated HCl. Water and Et₂O are added. The layers are separated and the top organic layer is washed with H₂O, dried over anhydrous MgSO₄ and concentrated in vacuo to give 2.21 g of yellow solid. Purification by chromatography using silica gel and eluting with increasing ratios of ethyl acetate/ hexane gives, after stripping, 0.77 g of yellow solid (36%) m.p. 190°-190.5° C.;

Following the procedures of Examples 7 and 8 above but using the appropriately substituted α-nitroacetophenone and 2,2-di(C₁-C₄ alkoxy)ethylamine yields the substituted α-(2,2-di(C₁-C₄ alkoxy)ethylamino)-β-nitrostyrene which is then converted to 3-nitro-2-(substituted)phenylpyrrole by treatment with HCl, HBr or CF₃CO₂H. Reaction of the thus formed substituted phenylpyrrole with sodium hypochlorite in dioxane yields the chloro analogs; whereas, reaction of the substituted phenylpyrrole with bromine in chloroform yields the bromine analogs.

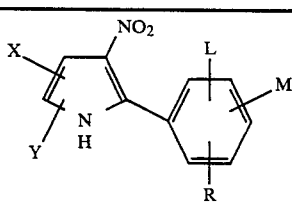

| L | M | R | X | Y | mp °C. |
|---|---|---|---|---|---|
| H | H | H | Cl | Cl | 190–190.5 |
| H | 4-Cl | H | Cl | Cl | 214–215 |
| H | 4-Cl | H | Br | Br | 203–204 (dec.) |
| H | H | H | Br | Br | 148.5–149 |
| 3-Cl | 4-Cl | C | Cl | Cl | 219–220 (dec.) |
| H | 4-Br | H | Cl | Cl | 222–223 (dec.) |
| H | H | 4-CF₃ | Cl | Cl | 166–168 |

EXAMPLE 9

4,5-Dichloro-2-(3,4-dichlorophenyl)-1-methyl-pyrrole-3-carbonitrile

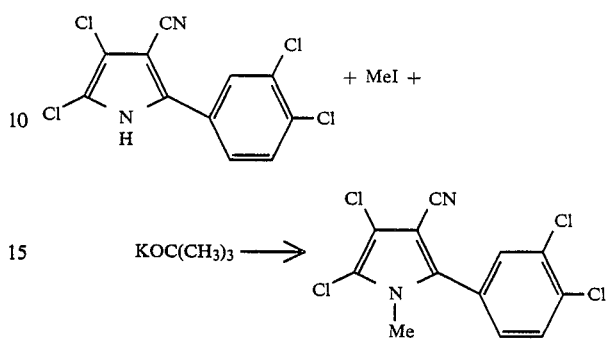

In a 100 mL flask, 2 g of 4,5-dichloro-2-(3,4-dichlorophenyl)pyrrole-3-carbonitrile in 60 mL dry THF gives a clear brown solution. 1 eq of KOtBu is added w/ stirring, this giving a clear solution after a few minutes. 1 eq of MeI is added by syringe and the solution is heated at reflux for 4 hours. It is then left to stir at RT overnight. The following day 50 mL of H₂O is added and the mixture extracted with 4×50 mL CHCl₃. The organic phases are combined, dried with MgSO₄, and concentrated. The resulting white solid is purified by flash chromatography on silica gel, using 50/50 EtOAc/hexane as an eluent. This gives 1.80 g of a white solid.

Yield=86% m.p.=154–156 deg. C.

Following the above procedure but substituting the appropriately substituted phenylpyrrole-3-carbonitrile or 3-nitro-2-(substituted)phenylpyrrole for 4,5-dichloro-2-(3,4-dichlorophenyl)pyrrole-3-carbonitrile yields the compounds shown below.

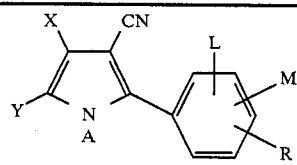

| A | L | M | R | X | Y | mp °C. |
|---|---|---|---|---|---|---|
| CH₃ | H | H | 4-Cl | Cl | Cl | 152–153 |
| C₂H₅OCH₂ | H | 3-Cl | 4-Cl | Cl | Cl | 128–130 |
| C₂H₅ | H | 3-Cl | 4-Cl | Cl | Cl | 137–138 |
| CH₃ | H | 3-Cl | 4-Cl | Cl | Cl | 154–156 |
| CH₃ | H | H | 4-CF₃ | Br | Br | 145–146 |
| C₆H₅—CH₂ | H | H | 4-CF₃ | Br | Br | 145–147 |
| C₆H₅—CH₂ | H | 3-Cl | 4-Cl | Cl | Cl | 95–96 |
| CH₂=CH—CH₂ | H | 3-Cl | 4-Cl | Cl | Cl | 69–70 |
| CH₂=C(Cl)—CH₂ | H | 3-Cl | 4-Cl | Cl | Cl | |
| CH≡C—CH₂ | H | 3-Cl | 4-Cl | Cl | Cl | 147–148 |
| CH₃SCH₂ | H | 3-Cl | 4-Cl | Cl | Cl | |
| C(CH₃)₃ | H | H | 4-CF₃ | Cl | Cl | |
| CH₃ | H | H | 4-CF₃ | Cl | Cl | 99–100 |
| CH₃SC₂H₅O | H | 3-Cl | 4-Cl | Cl | Cl | 74–75 |
| C₂H₅—OC—CH₂ | H | 3-Cl | 4-Cl | Cl | Cl | 118–120 |
| C₂H₅—OCH₂ | H | H | 4-CF₃ | Cl | Cl | 99–100 |
| CH₃ | H | H | 4-OCH₃ | Br | Br | 112–115 |

-continued

![structure with X, CN, L, M, R, Y, N, A]

| A | L | M | R | X | Y | mp °C. |
|---|---|---|---|---|---|---|
| CH₃ | H | H | 4-Cl | Br | Br | 197-201 |
| C₂H₅OCH₂ | H | H | 4-OCF₃ | Cl | Cl | 46-47 |
| CH₃ | H | H | 4-OCF₃ | Cl | Cl | 72-73 |
| C₆H₅—CH₂ | H | H | 4-OCF₃ | Cl | Cl | oil |
| C₂H₅OCH₂ | H | H | 4-Cl | Cl | Cl | — |
| HOCH₂CH₂ | H | 3-Cl | 4-Cl | Cl | Cl | 143-145 |
| NC | H | 3-Cl | 4-Cl | Cl | Cl | 251-252 |
| C₆H₅CH₂OCH₂ | H | 3-Cl | 4-Cl | Cl | Cl | 88-89 |
| Cl—⌬—O—CH₂ | H | 3-Cl | 4-Cl | Cl | Cl | 118-120 |
| IC≡C—CH₂ | H | 3-Cl | 4-Cl | Cl | Cl | 115-116 |
| CH₃ | H | H | 4-Cl | Br | CF₃ | 126-129 |
| C₂H₅OCH₂ | H | H | 4-Cl | Br | CF₃ | 91-92 |
| C₂H₅—OCH₂ | H | 3-Cl | 4-Cl | Cl | Cl | 118-120 |
| C₂H₅—OCH₂ | H | H | 4-Cl | Br | Br | 104-105 |
| C₆H₅—CH₂ | H | H | 4-Cl | Br | Br | 81-82 |
| CH₃ | H | H | 4-Cl | Br | Br | 197-201 |
| CN | H | H | 4-CF₃ | Cl | Cl | 138-139 |
| C₂H₅—OCH₂ | H | H | 4-CF₃ | Br | CF₃ | 104-105 |
| C₂H₅—OCH₂ | H | H | 4-CF₃ | H | CF₃ | 76-77 |
| C₂H₅OCH₂ | H | 3-Cl | 4-Cl | Br | CF₃ | 80-81 |

EXAMPLE 10

1-Benzyl-4,5-dibromo-2-(α,α,α-trifluoro-p-tolyl)pyrrole-3-carbonitrile

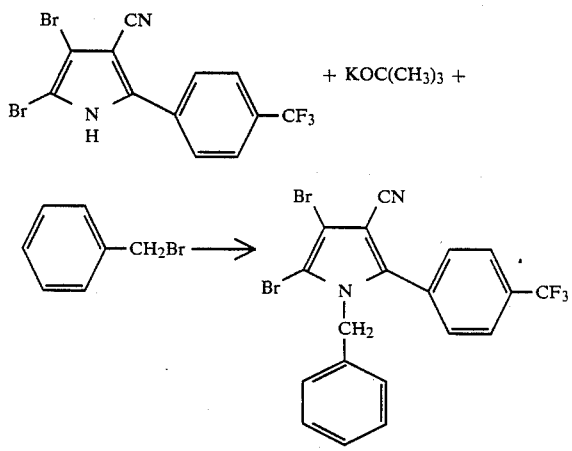

In a 100 mL flask, 1.5 g of 4,5-dibromo-2-(α,α,α-trifluoro-p-tolyl)pyrrole-3-carbonitrile is mixed with 50 mL dry THF to give a clear dark solution. 1 eq of KOtBu is added with stirring. After a few minutes the solution clears. Benzyl bromide (0.65 g) is added by syringe. The mixture is heated at reflux overnight. The following day TLC (50/50 EtOAc/hexane) indicates the presence of both starting material and product. The reaction is worked up in the following manner; 50 mL of water is added and the mixture is extracted with 4×50 mL CHCl₃. The organic phases are combined and washed with 4×50 mL 10% aq. NaOH. The organic phase is dried with MgSO₄ and stripped. This gives a brown solid which is crystallized from EtOAc/hexane.
Yield=0.75 g=40.7%
m.p.=145-147 deg.C. dec.

EXAMPLE 11

4,5-Dichloro-2-(3,4-dichlorophenyl)-1-(ethoxymethyl)-pyrrole-3-carbonitrile

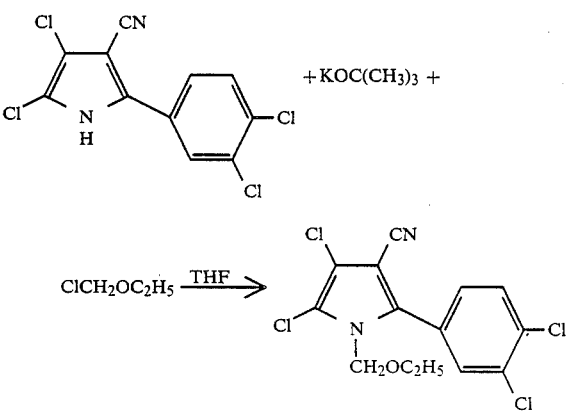

A sample of 4,5-dichloro-2-(3,4-dichlorophenyl)pyrrole-3-carbonitrile (1.0 g, 0.003 mole) is dissolved in 10 mL of dry tetrahydrofuran. To this solution is added potassium t-butoxide (0.37 g, 0.0033 mole) followed by chloromethyl ethyl ether (0.312 g, 0.0033 mole). The mixture is stirred for about 1 hour at room temperature and then poured into a large volume of water precipitating the product. The white solid is collected and dried to give 1.0 g (91%) with m.p. 128°-130°.

EXAMPLE 12

4-Chloro-3-cyano-2-(p-chlorophenyl)pyrrole

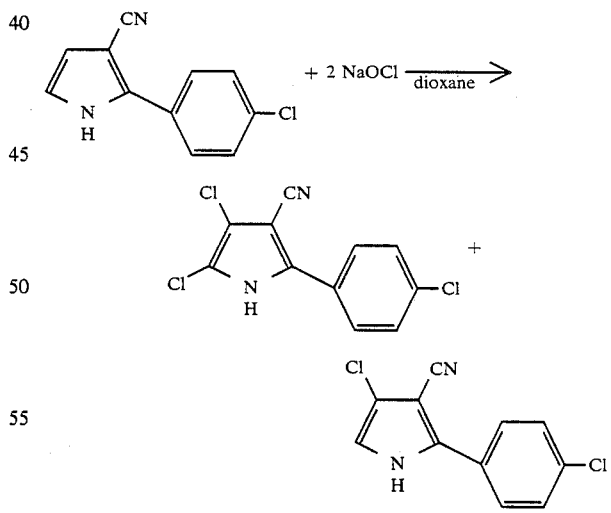

To a magnetically stirred 20° C. solution of 17.87 g (88.2 mmol, 1.00 eq) of 2-(p-chlorophenyl)-3-cyanopyrrole in 800 mL of dioxane is added dropwide 250.15 g (13.13 g real, 176.4 mmol, 2.00 eq) of 5.25 weight % bleach over a period of 30 minutes. After stirring at room temperature for a further 30 minutes, the reaction solution is poured into 2200 mL of water. The resulting mixture is vacuum filtered to remove a small amount of a black solid. The filtrate is acidified to pH 2 with concentrated HCl to produce a brown solid. This solid is vacuum filtered and the collected solids washed with water to give 22.41 g of a brown solid. This solid is treated with 100 mL of 5% aqueous sodium hydroxide to dissolve the bulk of the material while leaving a small amount of undissolved black solid. This black solid, dissolved into 100 mL of ethyl acetate, is washed with 75 mL each of 5% aqueous NaOH, water, and sat. aqueous NaCl. The ethyl acetate layer is dried (MgSO$_4$), treated with charcoal, filtered, and then rotary evaporated in vacuo to give 1.10 g (5.3% yield) of an orangish brown solid. This solid is recrystallized from an ethyl acetate chloroform mixture to give 0.51 g (2.4% yield) of an off-white solid of 4-chloro-3-cyano-2-(p-chlorophenyl)pyrrole. mp 251°–253.5° C.

EXAMPLE 13

Preparation of
5-bromo-2-(3,4-dichlorophenyl)pyrrole-3-carbonitrile

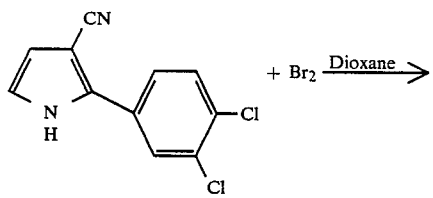

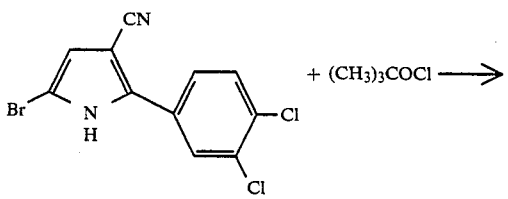

A sample of 2-(3,4-dichlorophenyl)pyrrole-3-carbonitrile (2.0 g., 0.008 mole) is dissolved in 100 mL of dioxane by warming to 40°–50°. Then the solution is cooled to 30° C. and bromine (1.3 g, 0.008 mole) is added. After stirring 1 hour at room temperature the solution is poured into water and a gray solid (2.2 g, 88%) is collected. The mp is 233°–236° C., decomposition.

In a similiar fashion one can prepare 5-bromo-2-(3,4-dichloro)-3-nitropyrrole starting with 2-(3,4-dichlorophenyl)-3-nitropyrrole.

EXAMPLE 14

Preparation of
5-bromo-4-chloro-2-(3,4-dichlorophenyl)pyrrole-3-carbonitrile

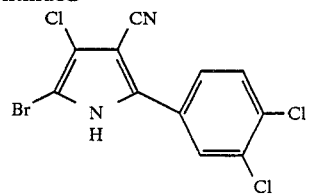

A sample of 5-bromo-2-(3,4-dichlorophenyl)pyrrole-3-carbonitrile (0.158 g, 0.005 mole) is dissolved in tetrahydrofuran (5 mL). An equivalent amount of t-butyl hypochlorite is added and the solution stirred overnight. The solution is poured into water and the precipitate (0.052 g, 30%) is collected. The mp is >275° C.

In a similiar fashion one can prepare 2-bromo-3-chloro-5-(3,4-dichlorophenyl)-4-nitropyrrole by starting with 2-bromo-5-(3,4-dichlorophenyl)-4-nitropyrrole.

EXAMPLE 15

Preparation of
5-bromo-4-chloro-2-(p-chlorophenyl)pyrrole-3-carbonitrile

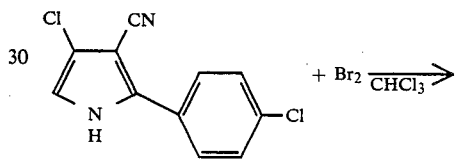

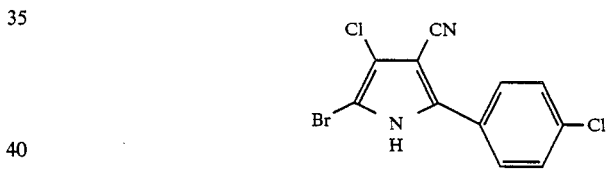

To a magnetically stirred 22° C. solution of 0.17 g (0.67 mmol., 1.00 equivalent) of 4-chloro-2-(p-chlorophenyl)pyrrole-3-carbonitrile in 100 mL of chloroform is added dropwise over a period of 30 minutes, a solution of 0.20 mL (0.62 g, 3.88 mmol., 5.79 equivalent) of bromine in 5 mL of chloroform. The addition produces no exotherm. After stirring at room temperature for 3¼ hours, the clear red reaction solution is evaporated in vacuo to give 0.28 g of an off-white solid. This solid is slurried with a hexanemethylene chloride mixture to give on vacuum filtration 0.23 g of an off-white fluffy solid. mp 262°–263° C.; dec.

EXAMPLE 16

Preparation of
5-chloro-4-bromo-2-(p-chlorophenyl)pyrrole-3-carbonitrile

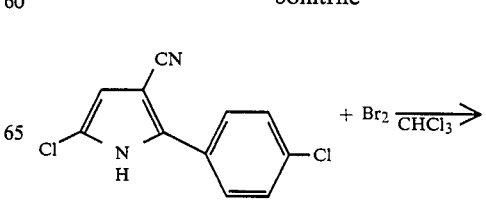

-continued

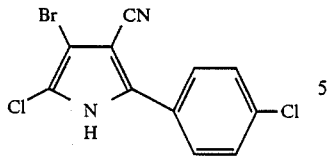

To a magnetically stirred 45° C. solution of 1.00 g (4.22 mmol., 1.00 equivalent) of 5-chloro-2-(p-chlorophenyl)pyrrole-3-carbonitrile in 300 mL of chloroform is added dropwise over a period of 30 minutes, a solution of 0.40 mL (1.24 g, 7.76 mmol., 1.84 equivalent) of bromine in 25 mL of chloroform. The addition produces no exotherm and towards the end of the addition, a small amount of a solid starts to precipitate. After stirring at room temperature for 19½ hours the reaction mixture is evaporated in vacuo to give 1.49 g of an orangish white solid. This solid is slurried with a hexane-methylene chloride mixture to give on vacuum filtration 1.33 g (100% yield) of a fluffy white solid. mp 250°–258° C., dec.

EXAMPLE 17
Preparation of 5-chloro-2-(p-chlorophenyl)pyrrole-3-carbonitrile

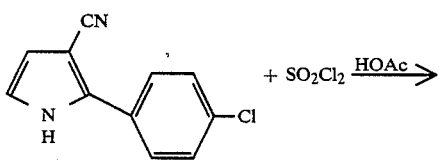

To a 35° C. magnetically stirred solution of 2.40 g (11.8 mmol., 1.00 equivalent) of 2-(p-chlorophenyl)pyrrole-3-carbonitrile, and 65 mL of glacial acetic acid is added dropwise by syringe 0.75 mL (1.26 g, 9.34 mmol., 0.79 equivalent) of sulfuryl chloride over a period of 5 minutes. Approximately 5 minutes after the completion of the addition, a solid precipitated out of the reaction solution. After stirring at room temperature for 45 minutes, the reaction mixture is filtered and the collected solid is washed well with cold acetic acid to give 2.08 g (74% crude yield) of an off-white solid. This solid is recrystallized from 75 mL of hot acetic acid to give 1.63 g (58% yield) of 97 wt % pure. Product mp 258.5°–261° C.

EXAMPLE 18
Preparation of 2-(3,4-dichlorophenyl)-1-methylpyrrole-3-carbonitrile

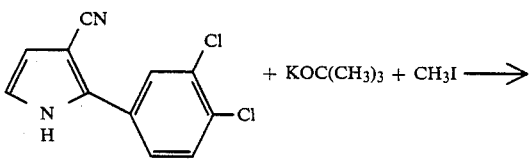

-continued

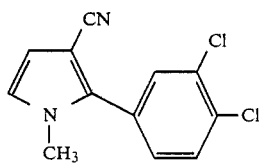

In a 100 mL flask, 2.0 g of 2-(3,4-dichlorophenyl)pyrrole-3-carbonitrile is dissolved in 50 mL of dry THF and 1 equivalent of potassium t-butoxide is added. This gives a slightly cloudy solution. One equivalent of methyl iodide is then added to the mixture by pipette. This leads to a slight lightening of the colour. A drying tube is attached to the flask and it is left to stir at ambient temperature overnight.

The next morning there is a slight light-coloured precipitate in the flask. 50 mL of water is then added and the solution becomes clear before a solid precipitates out of the solution. This solid is filtered out of the solution and compared to the starting material by TLC (25% ethyl acetate/hexane). This indicates a new single spot which is faster moving than the starting material. It is dried in a vacuum oven at 50 deg. C overnight. The product yield is 1.31 g or 62% yield and has a melting point of 140°–142° C.

EXAMPLE 19
Preparation of 4,5-dichloro-2-(3,4-dichlorophenyl)-1-methylpyrrole-3-carbonitrile

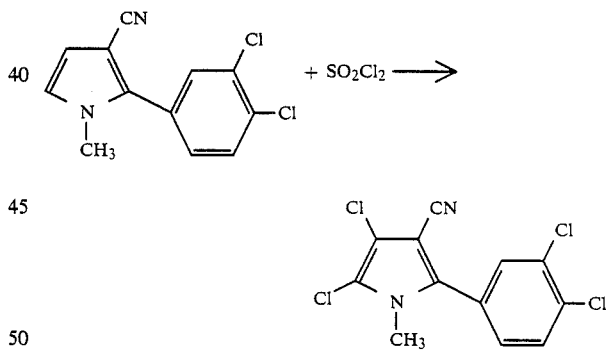

In a 50 mL round bottom flask, 0.5 g of 2-(3,4-dichlorophenyl)-1-methylpyrrole-3-carbonitrile is mixed with 35 mL of glacial acetic acid. The mixture is warmed slightly with a heat gun to dissolve all of the pyrrole.

To this clear solution is added 2 eq. of sulfuryl chloride by pipette. The solution is left to stir at room temperature for 12 hours.

After 12 hours the solution is poured into 50 mL of water, resulting in a white precipitate. This is filtered out and dried in a vacuum oven at 50° C. for 3 hours.

The resulting solid is identical by TLC, (25% ethyl acetate/hexane), and infrared analysis to the product of Example 9. Product yield is 0.36 (56%).

EXAMPLE 20

Preparation of
4,5-Dichloro-2-(3,4-dichlorophenyl)-1-(2-hydroxyethyl)-pyrrole-2-carbonitrile

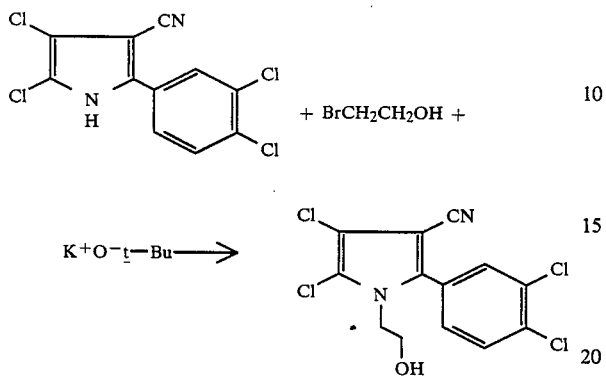

To a stirred mixture of 2.0 g (6.5 mmol) of 4,5-dichloro-2-(3,4-dichlorophenyl)-pyrrole-3-carbonitrile and 0.88 g (7.8 mmol) of potassium tert-butoxide heated at reflux in 50 mL of dioxane is added 0.98 g (7.8 mmol) of bromoethanol. The mixture is stirred at reflux for 12 hours, cooled, diluted with 50 mL of water, and extracted several times with chloroform. The combined chloroform extracts are dried over magnesium sulfate and concentrated in vacuo to leave a solid which, on warming and dissolving in ethyl acetate, deposits on cooling mostly starting pyrrole. Concentration of the mother liquor and recrystallization of the residual solid from 20% ethyl acetate in hexane gives 0.31 g of a white solid, mp 143°–145° C.; IR 5077A.

EXAMPLE 21

Preparation of
4,5-dichloro-2-(3,4-dichlorophenyl)pyrrole-1,3-dicarbonitrile

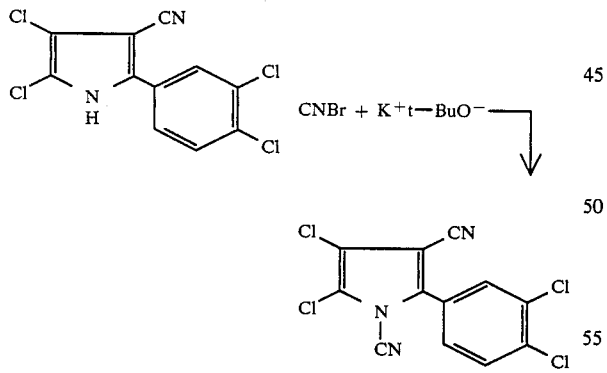

Potassium t-butoxide (617 mg, 55 mmol) is added in portions to a solution of 3-cyano-4,5-dichloro-2-(3,4-dichlorophenyl)pyrrole (1.52 g, 5 mmol) in anhydrous THF (20 mL). After 30 minutes, a solution of cyanogen bromide (583 mg, 5.5 mmol) in THF (1 mL) is added. The reaction mixture is stored at room temperature overnight. The solvent is removed in a rotary evaporator. The residue is treated with water and extracted with ethyl acetate. The organic layer is washed with water and saturated sodium chloride and dried ($MgSO_4$). Evaporation and crystallization of the residue from ethyl acetate gives while crystals (1.07 g); mp 250.5°–252.0° C.

EXAMPLE 22

Preparation of
4,5-Dichloro-2-(3,4-dichlorophenyl)-1-(3-iodo-2-propynyl)-pyrrole-3-carbonitrile

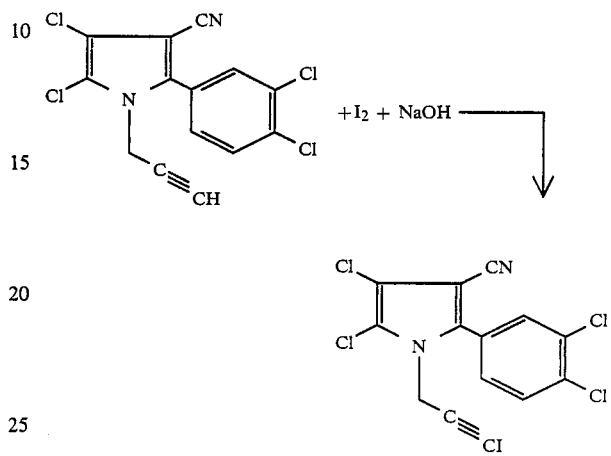

To a stirred mixture of 1.91 g (5.5 mmol) of 4,5-dichloro-2-(3,4-dichlorophenyl)-1-(2-propynyl)pyrrole-3-carbonitrile in 500 mL of methanol is added 69 mL of 10% aqueous sodium hydroxide and then 0.70 g (2.7 mmol) of iodine. The mixture is stirred for 12 hours and then acidified and diluted with 200 mL of water. The precipitated solids are collected and recrystallized from methanol to afford 0.51 g while crystals, m.p. 115°–116° C.

This reaction is also applicable to the conversion of any of the formula III, IV, V, VI or VII substituted N-alkynylarylpyrroles of the present invention to N-substituted iodo 3-4 alkynyl arylpyrroles of said invention.

EXAMPLE 23

Preparation of
2-(3,4-dichlorophenyl)-4,5-diiodopyrrole-3-carbonitrile

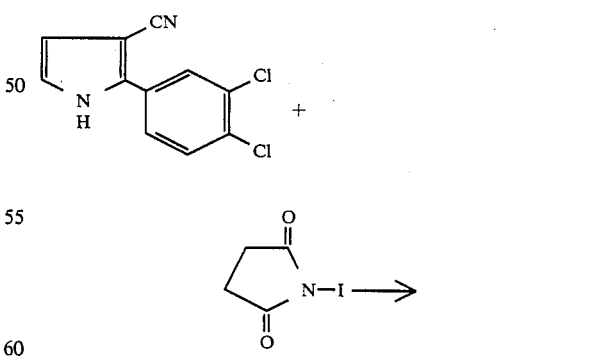

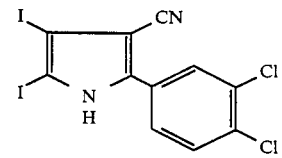

N-iodosuccinimide (5.7 g, 0.0254 mol,) is added slowly to a solution of 2-(3,4-dichlorophenyl)pyrrole-3-carbonitrile (3.0 g, 0.0127 mol) in 100 ml of THF. The reaction is stirred several hours at 25° C. until thin layer chromatography (silica gel; 100:100:1ether:petrolium ether:acetic acid) shows completion. The mixture is evaporated in vacuo to give a residue containing the pyrrole and succinimide. The crude solid is dissolved in 500 mL of ether and shaken with 5×400 mL of water to remove the succinimide. The ether is dried over Na$_2$SO$_4$ and evaporated in vacuo to leave 2.0 g (32.3%) of a grey-brown solid with mp >230° (loses purple vapors).

EXAMPLE 24

Preparation of 2-phenyl-1-pyrroline-4-carbonitrile

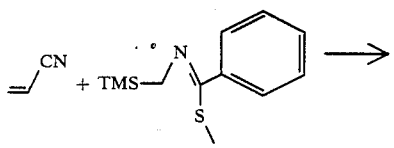

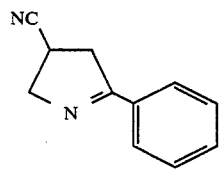

A solution of acrylonitrile (0.65 mL; 0.01 mol) and N-(trimethylsilyl)methyl-S-methyl-benzenethioimidate (2.4 g; 0.01 mol) in THF (100 mL) is cooled to −5° C. in an ice-acetone bath. Under a nitrogen purge, a solution of tetrabutylammonium fluoride (1.0 mL of a 1N solution in THF) and THF (20 mL) is added dropwise over 30 minutes The solution is stirred another 30 minutes at −5° C. , and then allowed to warm slowly to ambient. Stirring is continued another 18 hours, and then solvent is removed under reduced pressure. The residue is partitioned between ether/water and the water layer extracted with fresh ether. The combined organic layer is washed with water, then saturated sodium chloride. The solution is dried over MgSO$_4$, and cooling the filtrate causes precipitation of an off-white solid (1.2 g; 70% theoretical yield) whose spectral characteristics are identical to the material described by Tsuge [J. Org. Chem. 52, 2523 (1987)].

EXAMPLE 25

Preparation of 2-phenyl-pyrrole-4-carbonitrile

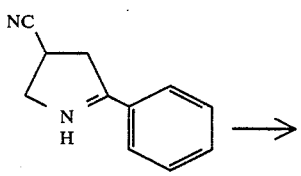

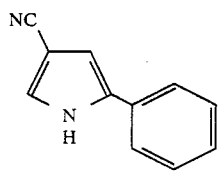

Under a nitrogen purge 2,3-dichloro-5,6-dicyano-1,4-bonzoquinone (0.23 g; 0.001 mol) and 2-phenyl-1-pyrroline-4-carbonitrile (0.17 g; 0.001 mol) is dissolved in 1,2-dimethoxyethane (13 mL) to form a clear orange solution. Pyridine (0.08 mL; 0,001 mol) is added in a single portion, causing a slight exotherm (to ca. 28° C.) and an immediate formation of a green/grey precipitate. The suspension is stirred at room temperature for 18 hours during which time much of the solvent evaporates. The brownish semi-solid residue is partitioned between ether and a half-saturated solution of sodium carbonate. The red-brown aqueous layer is extracted twice with ether and the combined ether layer is washed with fresh water, then saturated sodium chloride. After drying with MgSO$_4$, solvent is removed under reduced pressure to obtain a white semi-solid. This material was recrystallized from ethylene dichloride (DARCO treatment) to yield lavender crystals (0.1 g).

The identical product is obtained directly in a single step by condensing α-chloroacrylonitrile and N-(trimethylsilyl)methyl-S-methyl-benzenethioimidate using tetrabutylammonium fluoride catalysis (analogous to the preparation of 2-phenyl-1-pyrroline-4-carbonitrile described previously).

EXAMPLE 26

Preparation of 2,4-dibromo-5-phenyl pyrrole-3-carbonitrile

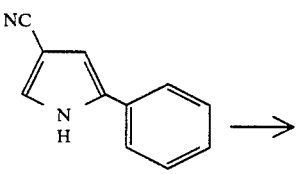

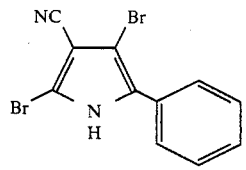

Under a nitrogen purge, a solution of bromine (0.6 mL; 0.012 mol) in CHCl$_3$ (5 mL) is added dropwise over 20 minutes to a stirring solution of 2-phenylpyrrole-4-carbonitrile (0.84 g; 0.05 mol) in CHCl$_3$ (20 mL). The resulting solution is stirred 18 hours at room temperature, then solvent is removed under reduced pressure to obtain a solid which is recrystallized from C$_2$H$_4$Cl$_2$ (DARCO treatment), yielding the desired final product (0.6 g), m.p.=239°-242° C.

By the procedure described in Example 24, 25 and 26, 2,4-dibromo-5-(p-chlorophenyl)pyrrole-3-carbonitrile, m.p. 270°-272° C. (dec.) is also prepared.

EXAMPLE 27

3′,4′-Dichloro-3-(1,3-dioxolan-2-yl)-propiophenone

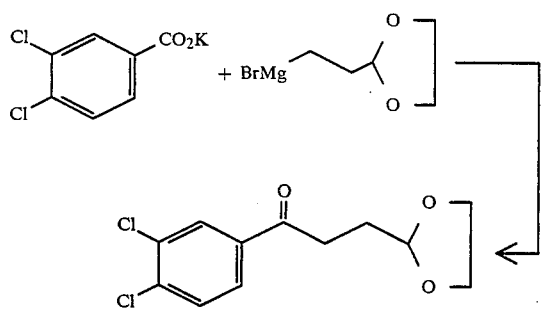

To a rapidly stirring mixture of magnesium turnings (0.64 g, 26 mmol) in 10 mL of tetrahydrofuran at 25° C. in a 100 mL three-neck round bottom flask equipped with a thermometer, a 60 mL addition funnel, and a nitrogen inlet is added dropwise 2-(2-bromoethyl)-1,3-dioxolane (4.7 g, 26 mmol) in 40 mL of tetrahydrofuran. The rate of addition is adjusted so as to maintain the reaction temperature below 50° C. The reaction is then allowed to stir for 1 hour at 25° C. 120 mL of tetrahydrofuran is mixed with potassium 3,4-dichlorobenzoate (5.0 g, 22 mmol) under a blanket of nitrogen. The Grignard solution is then quickly decanted away from the unreacted magnesium turnings, and added dropwise to the rapidly stirring potassium benzoate suspension. The reaction is then allowed to stir for 24 hours at 25° C. Fifty mL of diethyl ether and 15 mL of 3N hydrochloric acid are added to the reaction mixture and the layers separated. The organic layer is washed with saturated aqueous sodium bicarbonate until neutral followed by one washing with 10 mL of brine. Drying over sodium sulfate, and rotary evaporation yields a beige semisolid which is chromatographed over silica gel using 3:1 hexane-ethyl acetate as eluent to give the keto-acetal (4.3 g, 60%) as a white solid, m.p. 115°–117° C.

EXAMPLE 28

Preparation of 3-(3,4-dichlorobenzoyl)propionaldehyde

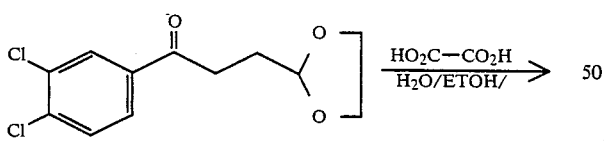

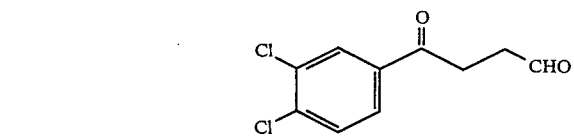

Ten grams (26 mmol) of 3′,4′-dichloro-3-(1,3-dioxolan-2-yl)-propiophenone is added to 30 mL of 0.2M oxalic acid (made by dissolving 0.9 g of oxalic acid dihydrate in 30 mL of water) and 5 mL of ethanol. The mixture is refluxed for 1 hour and then allowed to cool. Most of the ethanol is rotary evaporated off and 100 mL of diethyl ether is added along with 20 mL of saturated aqueous sodium bicarbonate. The layers are separated and the organic phase is dried over magnesium sulfate. Rotary evaporation yields a viscous yellow oil which is chromatographed over silica gel using 3:1 hexane-ethyl acetate to give the keto-aldehyde (6.3 g, 75%) as a white solid.

EXAMPLE 29

Preparation of 2-(3,4-dichlorophenyl)pyrrole

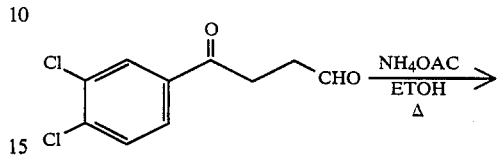

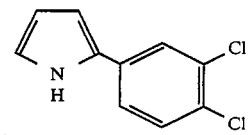

To a suspension of 3-(3,4-dichlorobenzoyl) propionaldehyde (6 g, 26 mmol) in 60 mL of absolute ethanol is added ammonium acetate (4 g, 52 mmol). The reaction is refluxed for 20 minutes and allowed to cool. Most of the ethanol is rotary evaporated and 200 mL of 1:1 dichloromethane-diethyl ether along with 50 mL of water is added. The layers are separated and the organic phase is dried over sodium sulfate. Rotary evaporation yields a dark brown oil which is chromatographed over silica gel using 3:1 hexane-ethyl acetate as eluent to give the pyrrole (4.6 g, 83%) as a light brown solid, m.p. 49°–51° C.

EXAMPLE 30

Preparation of 5-(3,4-dichlorophenyl)pyrrole-2-carboxaldehyde

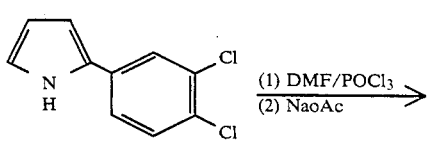

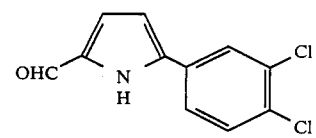

To 10 mL of dimethylformamide stirring under nitrogen in a 50 mL round bottom flask is added phosphorus oxychloride (0.6 mL, 6.5 mmol) dropwise via syringe. The solution warms and becomes light yellow in color. It is allowed to stir for 20 minutes before the portionwise addition of 2-(3,4-dichlorophenyl)pyrrole (1 g, 4.7 mmol). The beige suspension which results is allowed to stir for 30 minutes before being heated to 50° C. for 40 minutes. A solution of sodium acetate (10 g, 122 mmol) in 15 mL of water is added to the cooled reaction which is then allowed to stir for 20 minutes. A beige precipitate is filtered off from the reaction mixture and air-dried for 20 hours to give the essentially pure aldehyde (1.1 g, 95%), mp >200° C.

EXAMPLE 31

Preparation of 5-(3,4-dichlorophenyl)pyrrole-2-carbonitrile

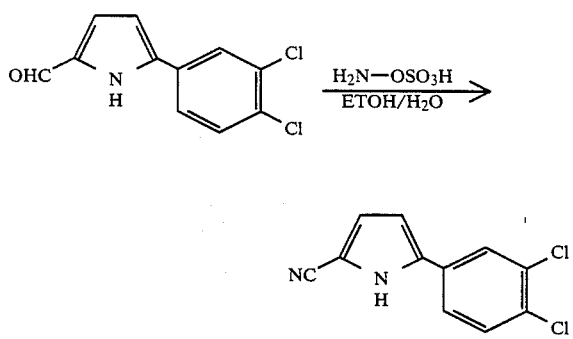

To a suspension of 5-(3,4-dichlorophenyl)pyrrole-2-carboxaldehyde (1.5 g, 6.2 mmol) in 20 mL of water and 20 mL of ethanol, is added hydroxylamine-O-sulfonic acid (0.7 g, 6.2 mmol). The reaction is refluxed for 1 hour during which time a gray precipitate appears. After being allowed to cool, the reaction is filtered to give essentially pure nitrile (1.5 g, 99%) as a gray solid, m.p. 170°–171° C.

EXAMPLE 32

Preparation of 3,4-dibromo-5-(3,4-dichlorophenyl)pyrrole-2-carbonitrile

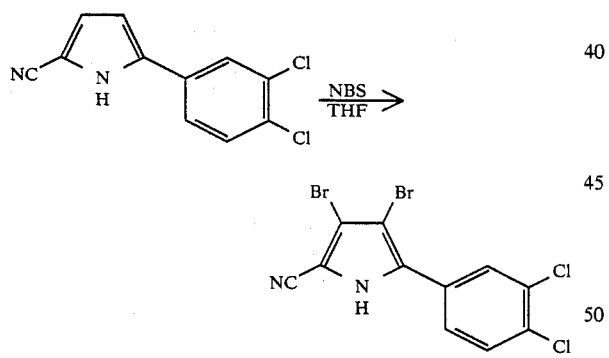

To a solution of 5-(3,4-dichlorophenyl)pyrrole-2-carbonitrile (0.5 g, 2.1 mmol) in 20 mL of tetrahydrofuran under nitrogen is added portionwise N-bromo-succinimide (0.8 g, 4.2 mmol). The reaction is stirred at 25° C. for 30 minutes before the addition of 10 mL of water and 40 mL of diethyl ether. The layers are separated and the organic layer dried over sodium sulfate. Rotary evaporation is followed by chromatography over silica gel using 3:1 hexane-ethyl acetate as eluent to afford the dibromopyrrole (0.5 g, 60%) as a brown solid, m.p. >250° C.

Also prepared by the procedure is 3,4-dichloro-5-phenylpyrrole-2-carbonitrile, m.p. 196°–200° C.

EXAMPLE 33

Preparation of 4-phenylpyrrole-3-carbonitrile

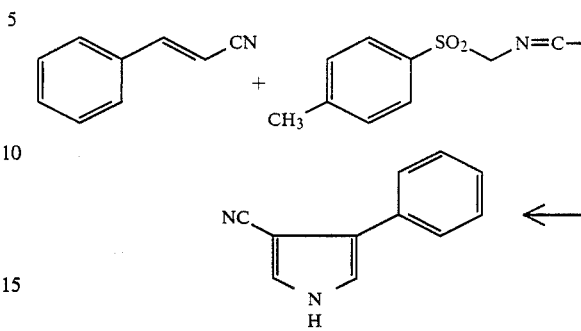

To a mixture of 5.0 g (39 mmol) of cinnamonitrile and 7.6 g (39 mmol) of (p-tolylsulfonyl)methyl isocyanide in 35 mL of DMSO and 65 mL of ether is added over a 20 minute period a suspension of 1.86 g of a 60% oil suspension of sodium hydride (1.11 g; 46 mmol) in mL of ether. The reaction mixture is maintained under nitrogen for an hour and then diluted with ether and water. The ether layer is separated, dried over magnesium sulfate, and concentrated in vacuo. The resulting oil is chromatographed on silica gel using 1:1 chloroform ethyl acetate to give 2.5 g of cream-colored solids. Recrystallization from ether-hexane affords 1.15 g, m.p. 123°–125° C.; NMR M86-1077.

Lit.: Tet. Letters 5337 (1972): m.p. 128°–129° C.

EXAMPLE 34

Preparation of 2,5-dichloro-4-phenylpyrrole-3-carbonitrile

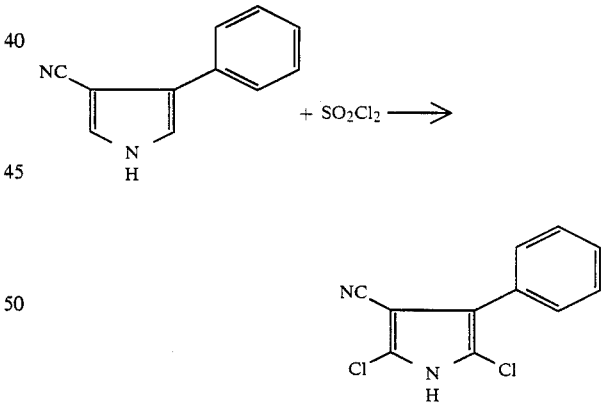

To a stirred mixture of 0.66 g (3.9 mmol) of 4-phenylpyrrole-3-carbonitrile in 20 mL of dry THF cooled to 6° C. with an ice-water bath is added from a syringe 0.66 mL (1.11 g; 8.2 mmol) of sulfuryl chloride over a 4 minute period. The mixture is maintained at 5°–10° C. for an additional 45 minutes and then stirred an additional 30 minutes with the ice bath removed. After the reaction mixture is poured into 80 mL of ethyl acetate and 40 mL of water, the organic phase is separated, washed with water, and dried over sodium sulfate. Filtration through a short column of silica gel, rinsing with ethyl acetate, and concentration of the combined filtrated in vacuo gives 0.95 g of dark solid. Recrystallization from chloroform gives 0.42 g of off-white crystals, m.p. 195°–196° C. (dec.).

Following the procedures of Examples 33 and 34, the following analogs are prepared. For the synthesis of 2,6-dibromo-4-(p-chlorophenyl)pyrrole-3-carbonitrile, the procedure of Example 33 is followed using bromine in dioxane to replace sulfuryl chloride and tetrahydrofuran.

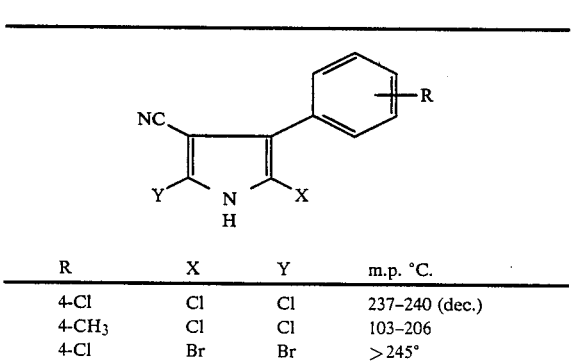

| R | X | Y | m.p. °C. |
|---|---|---|---|
| 4-Cl | Cl | Cl | 237–240 (dec.) |
| 4-CH₃ | Cl | Cl | 103–206 |
| 4-Cl | Br | Br | >245° |

EXAMPLE 35

Ethyl 4-(p-chlorophenyl)-pyrrole-3-carboxylate

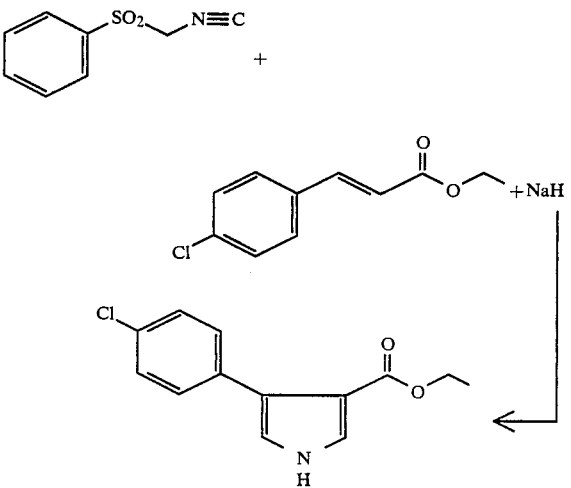

To a mixture of 5.63 g of a 60% sodium hydride/oil suspension in 200 mL of dry ether under nitrogen is added from an additional funnel a mixture of 23.5 g (122 mmol) of ethyl p-chlorocinnamate and 19.4 g (122 mmol) of (p-tolylsulfonyl)methyl isocyanide in solution in 180 mL of ether and 80 mL of dimethylsulfonide. The addition time is about 20 minutes and results in gentle refluxing of the mixture. After another 10 minutes stirring, the mixture is diluted with 100 mL of water. The mixture is extracted four times with ether which is then dried over magnessium sulfate followed by concentrated in vacuo. The resulting solid is recrystallized from ethylene dichlorite to give 7.8 g of crystals, m.p. 137°–138° C.

Concentration of the mother liquor for the crystallization leaves additional crude ester which is carried on to the saponification step.

EXAMPLE 36

Preparation of 3-(p-chlorophenyl)-pyrrole

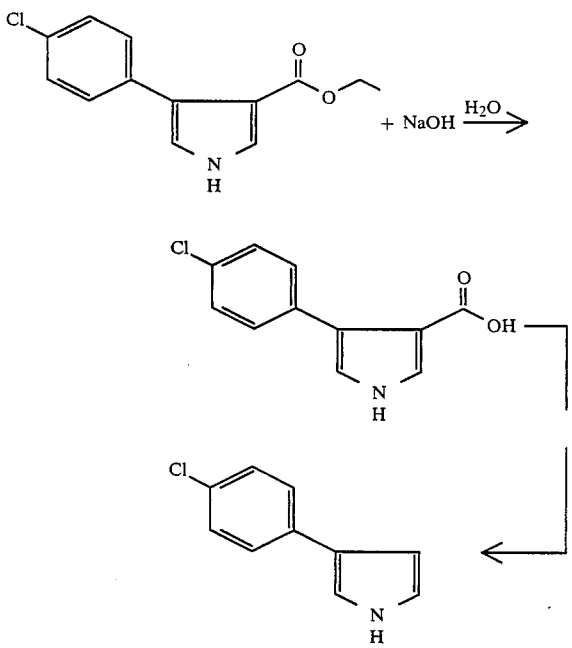

A mixture of 22.0 g of crude ethyl 4-(p-chlorophenyl)-pyrrole-3-carboxylate from the recrystallization mother liquor and the recrystallized product from the previous step is stirred at reflux with 150 mL of 10% aqueous sodium hydroxide for 2.5 hours. The mixture is cooled, extracted with ether, and acidified to give a precipitate which on collection and drying weighs 11.6 g.

A mixture of 10.5 g of the acid in 100 mL of β-ethanolamine is heated at reflux for three hours. After cooling, the mixture is poured over 400 mL of ice and the resulting mixture is extracted four times with chloroform. The chloroform solution, after drying over magnesium sulfate and treatment with activated charcoal, is concentrated in vacuo to leave a brown solid. Chromatography on silica gel using 1:1 ethyl acetate hexane gives 4.0 g of a white solid, m.p 117°–118° C.

EXAMPLE 37

Preparation of 3-(p-chlorophenyl)-pyrrole-2-caboxaldehyde

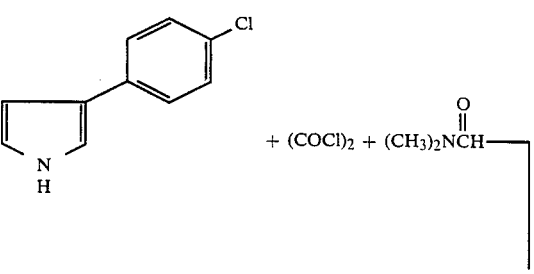

-continued

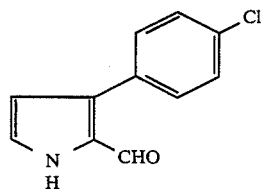

To a mixture of 0.86 g (12 mmol) of dimethylformamide in 10 mL of ethylene dichloride maintained under nitrogen and cooled in an ice bath is added 1.49 g (12 mmol) of oxalyl chloride in 10 mL of ethylene dichloride over a period of 25 minutes. The ice bath is removed, the mixture is stirred an additional 15 minutes and recooled in an ice bath. To this mixture is added 1.5 g (8.5 mmol) of 3-(p-chlorophenyl)-pyrrole in 25 mL of ethylene dichloride over a 20 minute period. The ice bath is removed and after an additional 30 minutes of stirring, the mixture is poured into 50 mL of ice-water and 6 mL of 50% sodium hydroxide. The resulting mixture is extracted with ether and with chloroform and the combined organic mixture is dried over magnesium sulfate and concentrated in vacuo. Purification of the resulting solid by chromatography on silica gel using 1:1 ethyl acetate hexane gives 0.63 g of off-white solid which is used directly for conversion to 3-(p-chlorophenyl)-pyrrole-2-carbonitrile.

EXAMPLE 38

Preparation of
3-(o-chlorophenyl)-pyrrole-2-carbonitrile

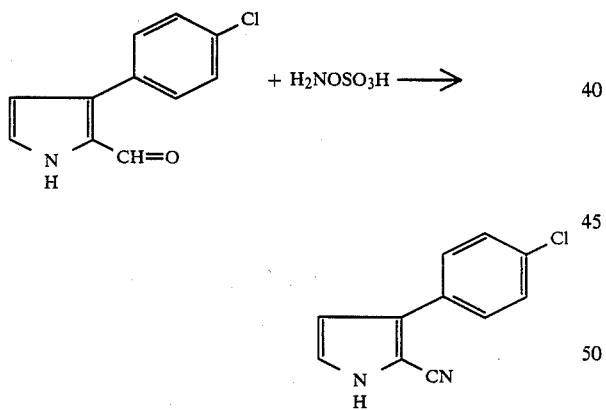

A mixture of 0.63 g (3.1 mmol) of 3-(p-chlorophenyl)-pyrrole-2-carboxaldehyde in 10 mL of water is stirred and ice-cooled while 0.52 g (4.6 mmol) of hydroxylamine-O-sulfonic acid in 10 mL of water is slowly added. After the addition, the cooling bath is removed and the mixture is heated for 25 minutes. On cooling, the resulting solid is collected and shown, by NMR, to be a mixture of product and starting aldehyde. This mixture is reacted in the same manner with an additional 0.49 g (4.2 mmol) of hydroxylamine-0-sulfonic acid in a total of 30 mL of water. The mixture is heated at 60°–70° C. for 2 hours. The mixture is cooled and the resulting solids are collected and purified by chromatography or silica gel using 1:1 ethyl acetate hexane to give 0.40 g of pink solid, m.p. 114°–115° C.

EXAMPLE 39

Preparation of
4,5-Dibromo-3-(p-chlorophenyl)-pyrrole-2-carbonitrile

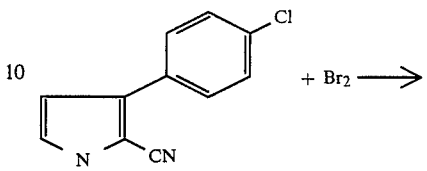

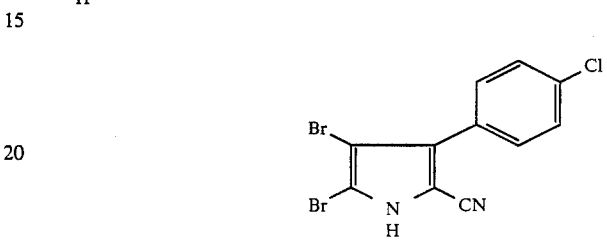

To a mixture of 0.40 g (2.0 mmol) of 3-(p-chlorophenylpyrrole)-2-carbonitrile in 25 mL of chloroform is added 0.63 g (4.0 mmol) of bromine. After 20 minutes, the precipitate which forms is collected and recrystallized from ethyl acetate to give 0.21 g of pink crystals, m.p >250° C.

EXAMPLE 40

Preparation of Ethyl
5-bromo-4-(p-chlorophenyl)pyrrole-3-carboxylate

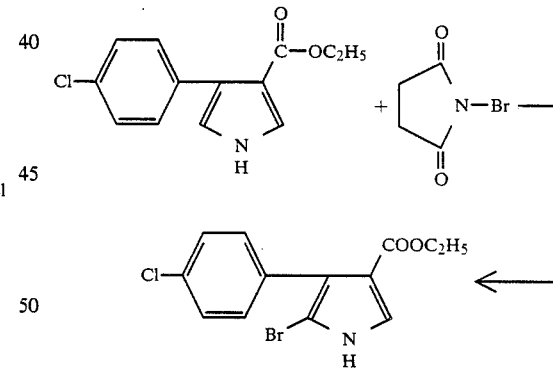

Ethyl 4-(p-chlorophenyl)pyrrole-3-carboxylate (1.6 g., 0.0064 mmol) is dissolved in tetrahydrofuran (40 mL). N-bromosuccinimide (1.14 g., 0.0064 mmol) is added in small portions at 25°–28° C. After the addition is complete, the solution is stirred overnight at room temperature. The solution is concentrated in vacuo and the solid residue partioned between water and ether. The ether layer is separated and dried over magnesium sulfate. Work-up of the ether extract leaves 1.9 g (90%) of a white solid which is purified by stirring with a mixture of 80/20 hexane/ethyl acetate. The insoluble solid (1.3 g, 62%) is collected and has m.p. 161°–164° C.

EXAMPLE 41

Preparation of
5-bromo-4-(p-chlorophenyl)pyrrole-3-carboxylic acid

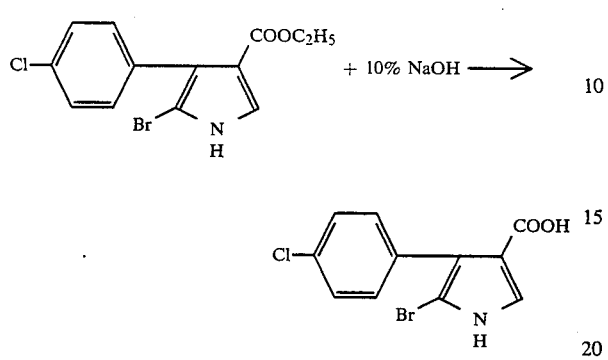

Ethyl 5-bromo-4-(p-chlorophenyl)pyrrole-3-carboxylate (15 g., 0.045 mmol) is added to 200 mL of 10% sodium hydroxide and the slurry heated to reflux. After everything appears to dissolve the mixture is refluxed an additional 40 minutes. The mixture is cooled, filtered and the filtrate acidified. The white precipitate (8.0 g, 58%) is collected and dried. The solid has m.p. >205° C. and an NMR ($d_6$-DMSO) which showed a pyrrole proton at 7.52 (d). The mass spectrum is also consistent for a monobrominated compound.

EXAMPLE 42

Preparation of 2-bromo-3-(p-chlorophenyl)pyrrole

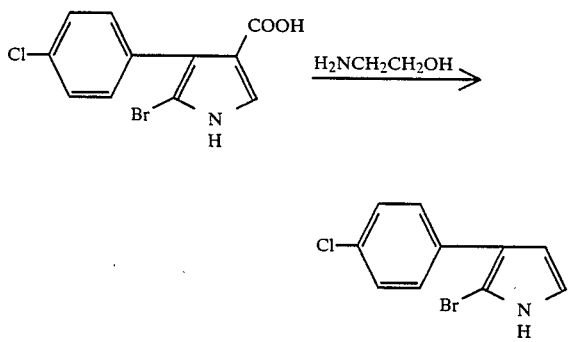

5-bromo-4-(p-chlorophenyl)pyrrole-S-carboxylic acid (8.0 g., 0.026 mmol) is added to aminoethanol (24 mL) and the slurry slowly warmed to 110°–120° C. and held at that temperature for 1 hour. The solution is cooled and poured into water and extracted with ether. The ether extract, by thin layer chromatography (75/25, hexane/ethyl acetate), shows a major fast moving spot and a slower moving minor component. Workup of the ether leaves a dark solid (4.0 g., 56%) which is 2-bromo-3-(p-chlorophenyl)pyrrole and is used immediately to prepare 5-bromo-4-(p-chlorophenyl)pyrrole-2-carbonitrile.

EXAMPLE 43

Preparation of
5-bromo-4-(p-chlorophenyl)pyrrole-2-carbonitrile

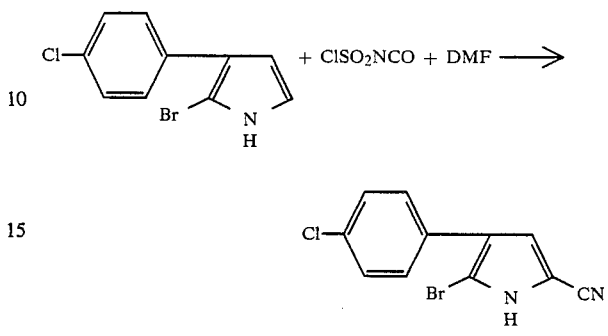

A freshly prepared sample of 2-bromo-3-(p-chlorophenyl)pyrrole (4.0 g., 0.015 mmol) is dissolved in dry dimethoxyethane (25 mL). Then while holding the temperature below 25° C., chlorosulfonyl isocyanate (3.08 g., 0.022 mmol) is added. After stirring overnight, the solution is treated with dimethylformamide (6 mL) and stirred for 3 hours. Finally, the solution is poured into water precipitating a brown solid (3.8 g, 90%). Dry column chromatography (80/20 hexane/ethyl acetate) yields 1.4 g (33%) of white solid with m.p. 202°–204° C.

EXAMPLE 44

Preparation of
3,5-Dibromo-4-(p-chlorophenyl)pyrrole-2-carbonitrile

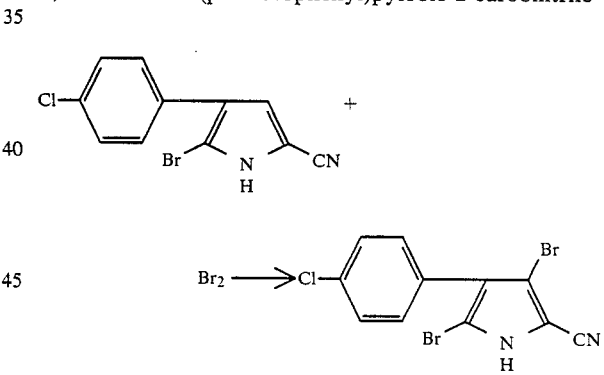

A sample of 5-bromo-4-(p-chlorophenyl)pyrrole-2-carbonitrile (2.2 g., 0.0078 mol) is dissolved in 30 mL of dry dioxane. The solution is heated with bromine (1.3 g., 0.008 mol) in dioxane (20 mL) and then stirred overnight at room temperature. The reaction mixture is poured into water precipitating a tan solid (2.6 g., 92%). A portion (1.6 g) is purified by flash chromatography using 75/25 hexane/ethyl acetate to give 0.8 g of grey solid with m.p. 191°–194° C.

EXAMPLE 45

Preparation of 3-(3,4-dichlorophenyl)-4-nitropyrrole

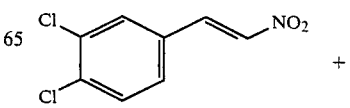

+

-continued

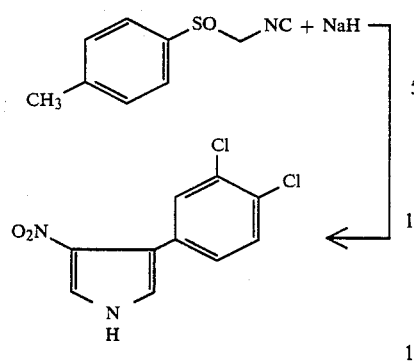

Sodium hydride (2.66 g of a 60% suspension in oil is rinsed with dry ether; 66 mmol) and suspended in 150 mL of dry ether. To this mixture is added over 15 minutes a mixture of 12.0 g (5.5 mmol) of 3,4-dichloro-β-nitrostyrene and 10.8 g (5.5 mmol) of (p-tolylsulfonyl)-methyl isocyanide in 50 mL of DMSO and 150 mL of ether. The mixture is stirred for 1.5 hours and then diluted with 150–200 mL of water and additional ether. The ether layer is separated, dried over magnesium sulfate, and concentrated in vacuo. The resulting 10.6 g of crude product is purified by chromatography on silica gel using a 4:1 mixture of chloroform and ethyl acetate. A 7.2 g solid fraction is recrystallized from chloroform-ethyl acetate-hexane to give 3.0 g of yellow solid, m.p. 187°–188° C. (dec.).

EXAMPLE 46

Preparation of 2,5-Dichloro-3-(3,4-dichlorophenyl)-4-nitropyrrole

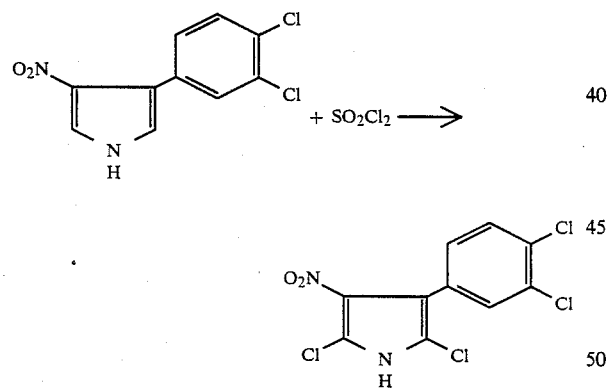

To a mixture of 3-(3,4-dichlorophenyl)-4-nitropyrrole 2.5 g, (9.7 mmol) warmed to about 40° C. in 200 mL of chloroform is added over one minute 2.95 g (22 mmol) of sulfuryl chloride. After another hour, the mixture is diluted with 100 mL of saturated sodium bicarbonate solution and 300 mL of ether. The organic layer is separated and dried over magnesium sulfate. Concentration, in vacuo, leaves a brown solid which is chromatographed on silica gel using 4:1 chloroform ethyl acetate. An orange solid fraction is recrystallized from chloroform and then rechromagraphed on silica gel using 4:1 chloroform ethyl acetate to yield 0.36 g of yellow solid, m.p. 193°–194° C.

Also prepared by procedure of Examples 45 and 46 above is 2,5-dichloro-3-nitro-4-phenylpyrrole, m.p. 193°–194° C.(dec.).

EXAMPLE 47

Preparation of 5-(p-chlorophenyl)pyrrole-2,4-dicarbonitrile

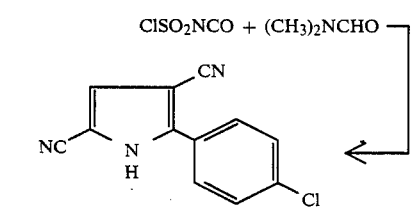

A sample of 2-p-chlorophenyl-3-cyanopyrrole, prepared by the method of Example 4, (3.0 g, 0.015 mole) is dissolved in 50 mL of dry dimethoxyethane. To this solution is added chlorosulfonyl isocyanate (3.39 g, 0.024 mole). The addition is exothermic and some cooling is necessary. After stirring 3 hours at room temperature, dimethylformamide (6–7 mL) is added and the solution is stirred 4 hours more. The solution is then poured into water precipitating a white solid (3.4 g, 100%). A sample (1.0 g) is purified by dissolving in ethyl acetate and then passing the solution through a 60 mL course filter funnel packed with silica gel. The filtrate is concentrated to yield 0.7 g of a white solid with m.p. 235°–240° C.

Following the procedure of Example 47, the following analogs are prepared:

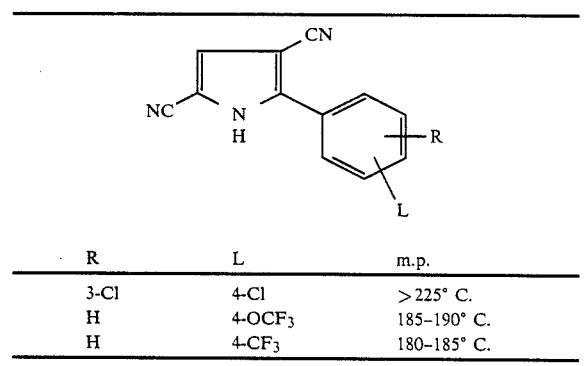

| R | L | m.p. |
|---|---|------|
| 3-Cl | 4-Cl | >225° C. |
| H | 4-OCF$_3$ | 185–190° C. |
| H | 4-CF$_3$ | 180–185° C. |

EXAMPLE 48

Preparation of 3-Bromo-5-(p-chlorophenyl)pyrrole-2,4-dicarbonitrile

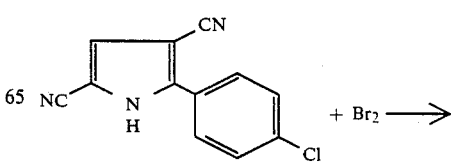

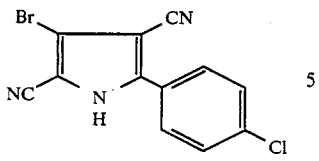

A sample of 5-(p-chlorophenyl)pyrrole-2,4-dicarbonitrile (1.0 g, 0.004 mole) is dissolved in 20 mL of dioxane and a solution of bromine (0.8 g, 0.005 mole) in dioxane (10 mL) is then added thereto. The solution is stirred several hours at room temperature and then poured into water precipitating a white solid (1.2 g, 100%). The solid has a m.p. >225° C. and a mass spectrum of a sample gives a pattern consistent with the desired structure.

Following the procedure set forth above in Example 48, the following additional compounds are prepared:

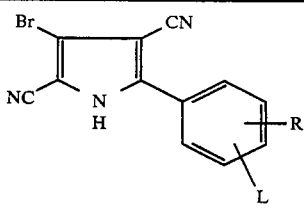

| R    | L      | m.p.        |
|------|--------|-------------|
| 3-Cl | 4-Cl   | >250° C.    |
| H    | 4-OCF$_3$ | 218–223° C. |
| H    | 4-CF$_3$  | 239–241° C. |

EXAMPLE 49

Preparation of bromofumaronitrile

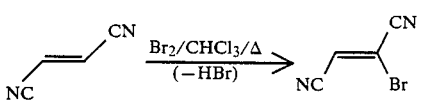

Under a nitrogen purge, fumaronitrile (15.6 g; 0.2 mol) in CHCl$_3$ (150 mL) is heated to reflux, resulting in a clear solution. A solution of bromine (5.3 mL; 0.2 mol) in CHCl$_3$ (25 mL) is added dropwise over 30 minutes, resulting in a slow decolorization and acidic (pH test paper) fumes being released. The solution is refluxed another 90 minutes, during which time most of the color has been discharged. The solution is cooled and solvent is removed under reduced pressure, leaving an amber oil (weight approximately theoretical for bromofumaronitrile). The oil is subjected to bulb-to-bulb distillation (0.2 mm Hg), maintaining the temperature below 120° C. (above that point, a rapid decomposition of material occurs). A semi-solid is obtained which slowly forms a waxy, amber solid, m.p.—43°–47° C.

EXAMPLE 50

Preparation of 2-phenyl-pyrrole-3,4-dicarbonitrile

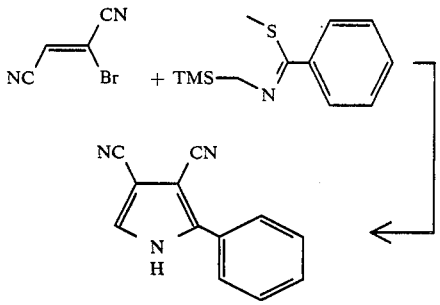

Under a nitrogen purge, a solution of bromofumaronitrile (4.7 g; 0.03 mol) and N-(trimethylsilyl) methyl-S-methyl-benzene-thioimidate (7.1 g; 0.03 mol) in hexamethylphosphoramide (HMPA) (35 mL) is stirred at room temperature. In a single portion, water (1.6 mL); 0.09 mol) is added, washed in with HMPA (10 mL). The solution almost immediately begins to exotherm, the temperature rapidly reaching 100° C. before subsiding The resulting dark red solution is allowed to stir at ambient temperature 20 hours. Pouring the reaction mixture onto an ice/water mixture results in a gummy material which slowly yields a discreet beige solid. This material is collected by filtration and washed with cold water and dried on the filter. After further drying (vacuum oven; 60° C.) the material is twice recrystallized from C$_2$H$_4$Cl$_2$ (DARCO treatment) to yield a white powder, m.p. 197°–200° C.

EXAMPLE 51

Preparation of 2-bromo-5-phenylpyrrole-3,4-dicarbonitrile

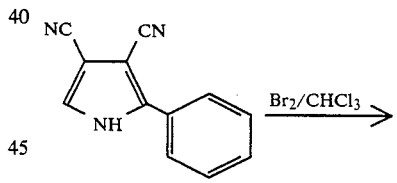

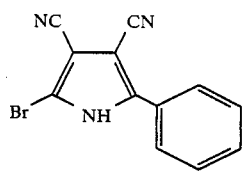

Under a nitrogen purge, 2-phenyl-pyrrole-3,4-dicarbonitrile (1.4 g; 0.0075 mol) is added to CHCl$_3$ (35 mL), much of the solid dissolving. A solution of bromine (0.4 mL; 0.008 mol) in CHCl$_3$ (5 mL) is added dropwise over 20 minutes. Initially the color is discharged rapidly, but as a new, gummy solid begins to precipitate, the color remains. After stirring 30 minutes at ambient, the mixture is brought to reflux, resulting in a much more discreet solid. After refluxing 90 minutes, the reaction mixture is cooled and an aliquot is removed and analyzed (HPLC), showing ca. 60% starting material still remaining. In a single portion fresh bromine (0.2 mL; 0.004 mol) is added, and refluxing continued another 45 minutes whereupon an aliquot shows 10% starting material remaining. Another fresh portion of bromine (0.2 mL; 0.004 mol) is added to the refluxing suspension and refluxing is continued another 30 minutes. The suspension is cooled and stirred 18 hours at room temperature. Solvent is removed under reduced pressure to yield a greenish solid which is extracted with hot CHCl₃, leaving behind a dark residue. The extract is treated with DARCO and filtered hot. The clear yellow filtrate quickly began to deposit a white precipitate. After cooling to −10° C., the white solid is collected by filtration, m.p. 225°–258° C.

EXAMPLE 52

Preparation of 2-(3,4-Dichlorophenyl)-5-nitropyrrole-3-carbonitrile

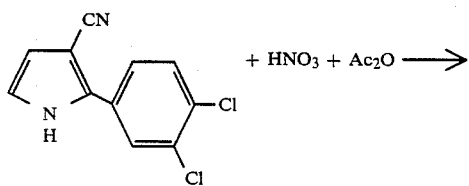

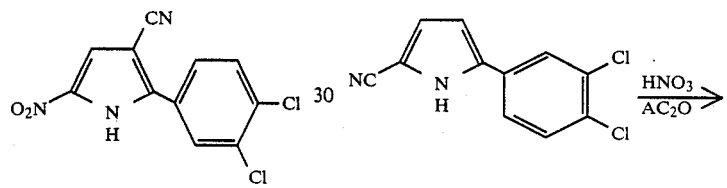

2-(3,4-Dichlorophenyl)pyrrole-3-carbonitrile (3.0 g, 0.013 mole) is added to acetic anhydride (50 mL) and 90% nitric acid (0.6 ml) with very little exotherm The mixture is slowly warmed to 30° and is then held at 30°–33° until everything goes into solution. Gradually a new solid precipitates. The mixture is stirred for 2 to 3 hours at room temperature and then poured into water and ice to decompose the acetic anhydride. After stirring 1 hour the mixture is filtered and the solid (2.9 g, 82%) collected and dried. A portion (1.5 g) is purified by column chromatography on silica gel using 75/25 hexane/ethyl acetate for elution to give 0.7 g of yellow solid with m.p. 228°–231°.

By the same procedure, starting with 2-(p-chlorophenyl)pyrrole-3-carbonitrile, 2-(p-chlorophenyl)-5-nitropyrrole-3-carbonitrile is obtained, m.p. 201°–206° C.

EXAMPLE 53

Preparation of 4-Bromo-2-(3,4-dichlorophenyl)-5-nitropyrrole-3-carbonitrile

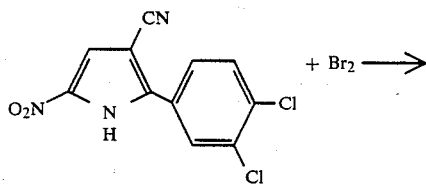

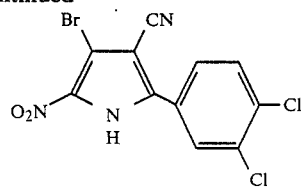

2-(3,4-Dichlorophenyl)-5-nitropyrrole-3-carbonitrile (0.5 g, 0.0017 mol) is dissolved in dry dioxane (10 mL). To this solution is added bromine (0.28 g, 0.0017 mole) in dioxane. After stirring overnight, the solution is poured into water precipitating a tan solid (0.54 g, 88%). Recrystallization from acetonitrile (5 mL) gives 0.26 g of tan solid with m.p. 195°–200° C.

Following the above procedure of Example 53, but starting with 2-(p-chlorophenyl)-5-nitropyrrole-3-carbonitrile gives 4-bromo-2-(p-chlorophenyl)-5-nitropyrrole-3-carbonitrile, m.p. 180°–185° C.

EXAMPLE 54

5-(3,4-Dichlorophenyl)-4-nitropyrrole-2-carbonitrile

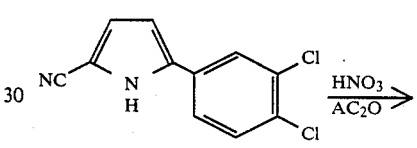

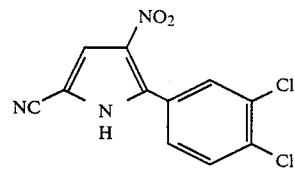

To a suspension of 5-(3,4-dichlorophenyl)pyrrole-2-carbonitrile (1.2 g, 5.1 mmol) in 25 mL of acetic anhydride at 30° under nitrogen, is added dropwise 90% nitric acid (0.3 mL, 5.1 mmol). The reaction exotherms to 45° C. and becomes a green solution. After being allowed to stir for 2 hours the reaction is poured into 50 mL of water and stirred vigorously for 5 minutes. The beige precipitate which results is filtered off and dissolved in a minimum amount of acetone. Chromatography over silica gel using 3:1 hexane-ethyl acetate affords the nitropyrrole (1.2 g, 84%) as an off-white solid, m.p. >200° C.

EXAMPLE 55

3-Bromo-5-(3,4-dichlorophenyl)-4-nitropyrrole-2-carbonitrile

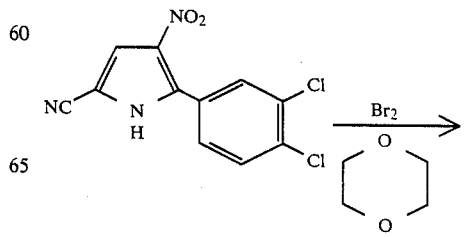

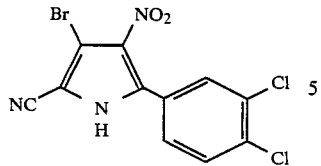

To a suspension of 5-(3,4-dichlorophenyl)-4-nitropyrrole-2-carbonitrile (0.6 g, 2.1 mmol) in 10 mL of dioxane at 25° C., under nitrogen, is added dropwise a solution of bromine (0.3 g, 2.1 mmol) in 5 mL of dioxane. The reaction is allowed to stir overnight. Addition of 50 mL of water causes precipitation of a yellow solid which is collected and vacuum oven dried (50 mm Hg, 45° C.) to afford the brominated pyrrole (0.7 g, 90%) as a light yellow solid, m.p. >200° C.

EXAMPLE 56

4-(p-chlorophenyl)-2-(trifluoromethyl-2-oxazolin-5-one

In a single portion, trifluoroacetic anhydride, (1.7 mL; 0.012 mol) is added to powdered 2-(p-chlorophenyl)glycine (11.4 g; 0.06 mol), causing an immediate exotherm to about 40° C., a yellow color forming on the surface of the solid. As the mixture is slowly heated to 70° C., more of the solid dissolves to an orange/amber oil. All the solid dissolved in approximately 2 hours, and heating is continued another hour. Solvent is removed under reduced pressure on a rotary evaporator. Toluene is twice added and removed under reduced pressure, but the odor of trifluoroacetic acid is still evident. This yellow semi-solid (yield theoretical; purity >90% by HPLC) is the above-identified compound and is used in the next step without further purification.

EXAMPLE 57

Preparation of 2-(p-chlorophenyl)-5-(trifluoromethyl)pyrrole-3-carbonitrile 4-(p-chlorophenyl)-2-(trifluoromethyl)-2-oxazolin-5-one (2.5 g; 0.01 mol) is dissolved in nitromethane (50 mL). In a single portion, 2-chloroacrylonitrile (8.0 mL; 0.10 mol) is added to the solution, and the resulting solution is stirred 18 hours at reflux under a nitrogen atmosphere. Cooling the red/brown solution to −5° C. in an ice-acetone bath causes the formation of a precipitate which is collected by filtration and washed with a small portion of cold nitromethane. The resulting tan solid is recrystallized from hot ethylene dichloride yielding the product as white crystals (1.8 g; 56% theory), m.p. 238°–241° C. (dec.).

By utilizing the appropriate arylglycine in the procedure of Example 55 and following the procedure of this Example, the following 2-aryl-5-(trifluoromethyl)pyrrole-3-carbonitrile were prepared:

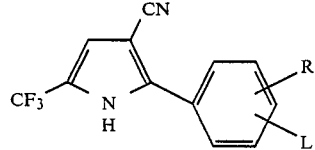

| R | L | m.p. °C. |
| --- | --- | --- |
| H | H | 215–218 |
| H | 4-CH$_3$ | 191–193 |
| H | 4-OCH$_3$ | 168–180 (dec.) |
| 3-Cl | 4-Cl | 245–246 (dec.) |
| H | 4-CF$_3$ | 218–219 |

EXAMPLE 58

Preparation of 4-Bromo-2-(p-chlorophenyl)-5-(trifluoromethyl)pyrrole-3-carbonitrile Under a nitrogen purge, a suspension or 2-(p-chlorophenyl)-5-(trifluoromethyl)pyrrole-3-carbonitrile (1.6 g; 0.005 mol) in acetic acid (25 mL) is heated, all the material dissolving to a clear solution at about 60° C. A solution of bromine (0.8 mL; 0.015 mol) in acetic acid (10 mL) is added dropwise over 15 minutes to the refluxing solution. The solution is refluxed 6 hours then allowed to stir 18 hours at room temperature. The HPLC of the reaction mixture shows about 80% conversion to product. The mixture is heated back to reflux and more bromine (0.5 mL; 0.01 mol) in acetic acid (5 mL) is added dropwise. After refluxing another 3 hours, the aliquot shows >95% conversion to product. The reaction is cooled, and solvent removed under reduced pressure on a rotary evaporator to obtain a dark grey solid. Toluene is added to the mixture and removed under reduced pressure, but the odor of acetic acid still remains. The entire material is dissolved in hot toluene (75 mL) to a turbid solution which is treated with DARCO filter and filtered. The light pink solution deposits a white solid upon cooling to ambient. After cooling in the freezer, the solid is collected by filtration, washed with hexanes, and dried on the filter. Further drying in a vacuum oven at 45° C. provides the product (1.2 g; app. 60% theoretical); m.p. 247°–250° C.(dec.)

By brominating the appropriate 2-aryl-5-(trifluoromethyl)pyrrole-3-carbonitrile, obtained by the procedure of Example 57, according to the above recipe, the following additional examples are prepared:

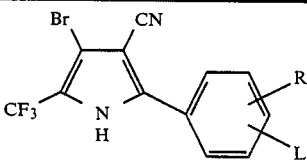

| R | L | m.p. °C. |
| --- | --- | --- |
| H | H | 235–238 |
| H | 4-CH$_3$ | 244–245 |
| 3-Cl | 4-Cl | 218–223 |
| H | 4-CF$_3$ | 225–226 |

EXAMPLE 59

Preparation of 2-(4-chlorophenyl)-5-trifluoromethylpyrrole-3,4-dicarbonitrile

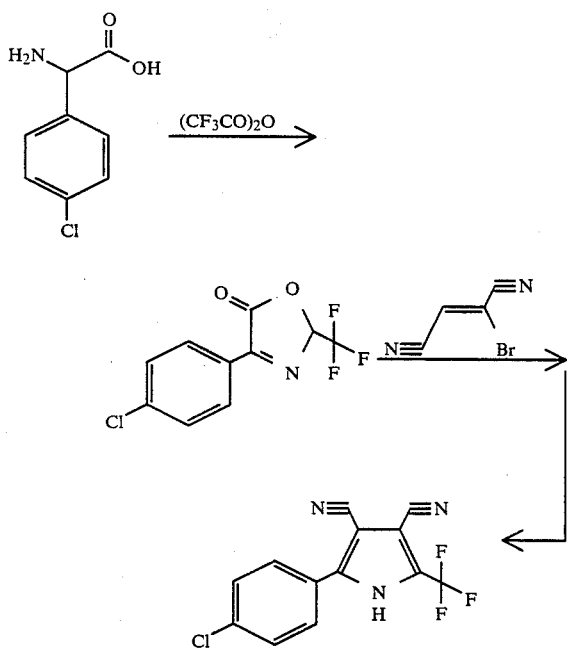

Trifluoroacetic anhydride (3.1 mL; 0.022 mol) is added in a single portion to (4-chlorophenyl)glycine (2.0 g; 0.011 mol), causing an immediate yellow color and some refluxing. The mixture is slowly heated to reflux, causing all the material to dissolve to a yellow-/orange solution which is heated 2 hours further. The reaction mixture is cooled, and solvent removed under reduced pressure. Toluene, is twice added and removed under reduced pressure to yield a very thick oil ($V_{CO}=1800$ cm$^{-1}$). This residue is dissolved (some insolubles) in CH$_3$NO$_2$ (40 mL) and bromofumaronitrile (2.7 g; 0.018 mol) is added in a single portion. The resulting solution is heated at reflux 18 hours, yielding a dark red solution. Solvent is removed under reduced pressure and the dark residue is dissolved in CH$_2$Cl$_2$, some insolubles being removed by filtration. The material is fractionated via dry column chromatography (silica gel; 3% 2-PrOH in CH$_2$Cl$_2$), and appropriate fractions are taken. Evaporation of one fraction yields the desired compound as a yellow solid which is recrystallized from CH$_3$CN (DARCO treatment) to yield a pale yellow solid (0.2 g). m.p. =238°–241° C. (some dec).

EXAMPLE 60

Evaluation of test compounds as molluscicidal agents

In this test a 5.0% bait of 4,5-dichloro-2-(3,4-dichlorophenyl)pyrrole-3-carbonitrile is prepared by mixing 0.05 gms of the technical grade carbonitrile with 0.95 gms of a crushed wheat and molasses blend. A 5.0% bait of 3,5-dimethyl-4-(methylthio)phenyl) methylcarbamate, i.e. methiocarb, is also prepared in the manner described above and is used as a standard. In the test 1.0 gms of bait is placed in the center of a moist filter paper used to line each 10 cm diameter, plastic petri dish. Two controls are set up using untreated bait. The first replicate of each treatment is infested with 5 field collected "large spotted" slugs. The second replicate of each treatment is infested with 3 field-collected *Arion subfuscus*. Mortality readings are taken periodically after the test is initialed. Data obtained are reported below.

| Compound | Percent Mortality | | | | | |
| --- | --- | --- | --- | --- | --- | --- |
| | 1 DAT | | 2 DAT | | 3 DAT | |
| | A | B | A | B | A | B |
| 4,5-Dichloro-2-(3,4-dichlorophenyl)pyrrole-3-carbonitrile | 40 | 0* | 60 | 0 | 100 | 0 |
| Methiocarb | 80** | 100 | 100 | — | — | — |
| Untreated Control | 0 | 0 | 0 | 0 | 0 | 0 |

A = *Limax maximus*
B = *Arion subfuscus*
\* = Slugs in this petri dish had gray blotches on all individuals.
\*\* = The remaining slug appeared moribund.

From the above data it can be seen that 4,5-dichloro-2-(3,4-dichlorophenyl)pyrrole-3-carbonitrile is molluscicidal against the spotted species of slug. Although the *Arion subfuscus* slugs were not killed in this test, they did become discolored.

EXAMPLE 61

Evaluation of test compounds as molluscicidal agents

A 5% bait of each test compound is prepared by mixing 0.10 gms of technical material with 1.90 gms of a bait consisting of 46% unprocessed bran, 6% molasses, and 48% water. Two test arenas are set up for each treatment by placing 2.0 gms of the bait into a lid from a one-ounce jar, and placing the lid into a moist filter-paper lined, eight-ounce, wax-paper cup. The number and type of slug placed in each container is indicated in the following table. A plastic lid, with pin holes through it, is placed over the top of each cup. The test is set up and infested with field-collected slugs. Mortality readings are taken after 1, 3 and 4 days after the tests are initiated. Slugs that do not respond to prodding are considered dead. Slugs that respond much more slowly than the untreated control slugs are considered moribund.

Data obtained are reported below.

| Compound | Number and Type of Slugs Per Replicate | |
| --- | --- | --- |
| | A | B |
| 2,3-Dichloro-5-(p-chlorophenyl)-4-nitrophenol | 5-*Limax maximus* | 5-*Arion subfuscus* |
| Methiocarb | 5-*Arion subfuscus* | 5-*Arion subfuscus* |
| Untreated Control | 5-*Limax maximus* | 5-*Arion subfuscus* |

| Compound | Percent Mortality | | | | | |
| --- | --- | --- | --- | --- | --- | --- |
| | 1 DAT | | 2 DAT | | 3 DAT | |
| | A | B | A | B | A | B |
| 2,3-dichloro-5-(p-chlorophenyl)-4-nitropyrrole | 20* | 40** | 60* | 80 | 60 | 100 |
| Methiocard | 80* | 100 | 100 | — | — | — |
| Untreated Control | 0 | 0 | 0 | 0 | 0 | 0 |

\* = The remaining slugs appeared moribund.
\*\* = One of the remaining slugs appeared moribund.

EXAMPLE 62

Evaluation of test compounds as molluscicidal agents

A 5% bait of each test compound is prepared by mixing 0.10 gms of technical material with 1.90 gms of a bait consisting of 46% unprocessed bran, 6% molasses, and 48% water. One test arena is set up for each treatment by placing 2.0 gms of the bait into a lid from a one-ounce jar, and placing the lid into a moist filter-paper lined, eight-ounce, wax-paper cup. Each cup is infested with 5, field-collected slugs, *Arion subfuscus*. A plastic lid, with pin holes through it, was placed over the top of each cup. The test is set up and infested with the field-collected slugs. Mortality readings are taken after 1, 2, 3 and 4 days. Slugs that do not respond to prodding are considered dead. Slugs which respond much more slowly than the untreated control slugs are considered moribund.

| Compound | Percent Mortality | | | |
|---|---|---|---|---|
| | 1 DAT | 2 DAT | 3 DAT | 4 DAT |
| 2,3-Dichloro-4-nitro-5-phenyl-pyrrole | 0** | 60 | 60 | 80* |
| 1-Benzyl-4,5-dichloro-2-(3,4-dichlorophenyl)-pyrrole-3-carbo-nitrile | 20** | 40** | 100 | — |
| Methiocarb | 0** | 40* | 80 | 80* |
| Untreated Control | 0 | 0 | 0 | 0 |
| 1-Benzyl-4,5-dichloro-2-(3,4-dichlorophenyl)-pyrrole-3-carbo-nitrile | 0* | 20* | 100 | — |
| 2,3-Dibromo-5-(p-chlorophenyl)-4-nitropyrrole | 0 | 0 | 60* | 100 |
| 2-(p-Bromophenyl)-4,5-dichloro-3-nitropyrrole | 0 | 100 | — | — |
| 2,3-Dichloro-4-nitro-5-(α,α,α-trifluoro-p-tolyl)pyrrole | 60* | 100 | — | — |
| Methiocarb | 0* | 0* | 60* | 100 |
| Untreated Control | 0 | 0 | 0 | 0 |

EXAMPLE 63

Slug test

Slugs are collected from the field and placed in an ice cream cup with a plastic lid which has holes for aeration. Three species are collected; *Limax maximus*, *Arion subfuscus* and *Deroceras raticulatum*. A slug bait is prepared having the following composition:

| 1 oz. metaldehyde | = 28.4 ml or 28.4 mg | = 1.78 mg |
|---|---|---|
| 2 lb. bran | = 98. g | = 56.76 g |
| 4 tbsp. molasses | = 57.8 ml | = 3.61 ml* |
| 1 pt. water | = 473 ml | = 29.56 ml |

This recipe is used as a bait with test compounds added separately at 5%. 50 mg of compound is added to 950 mg of bait. This is 25 times greater than the reccomended dosage using metaldehyde as the control agent.

One species of slug is used in these tests, *Arion subfuscus*. Three slugs are used per treatment. All compounds are tested at 5% concentration in the bait. Nine cm petri dishes are used with one moistened (one ml $H_2O$) Whatman #1 filter paper in each. The treatment diet is placed directly on the filter paper and the slugs placed in the cups with the results obtained reported below.

| Compound | % MORTALITY/COMMENTS | | |
|---|---|---|---|
| | 24 Hours | 48 Hours | 6 Days |
| Trifenmorph | 0 | 0 | 0 |
| Niclosamide | 0 | 0 | 0 |
| Methiocarb | 67/** | 100 | 100 |
| 2,3-Dichloro-5-(p-chlorophenyl)-4-nitropyrrole | 67/** *** | 100 | 100 |
| untreated Check | 0 | 0 | 0 |

**Enlarged anterior
***Mucous secretion

Results:

The pyrrole is as active as methiocarb, but acts differently in that it is a de-mucosing agent. This observed activity of the pyrrole would increase dessication and cause the animal to be more vilnerable to its enviornment.

EXAMPLE 64

Land Snail Experiment with Arylpyrroles

Procedure:

*Bulimulus maria* (Land Snails from Carolina Biological Supply Company, Code L480) are tested in 30 ml wide mouth jars. A 5% bait with cornmeal is used i.e. 25 mg of compound mixed in 450 mg cornmeal. The bait is moistened every two days. One snail is added to each jar and the cups are loosely placed on top. Fecal matter indicate feeding. Mortality is observed by probing the animal with a spatula. If the animal is alive contractions are evident. Oozing and/or complete withdraw into the shell indicates mortality.

Observations:

| Compound | 18 Hrs. | 72 Hrs. | 1 Week | 10 Days |
|---|---|---|---|---|
| 2,3-Dichloro-5-(p-chlorophenyl)-4-nitropyrrole | A | A | D | D |
| 4,5-Dichloro-2-(3,4-dichloro-phenyl)pyrrole-3-carbonitrile | A, Z | A | A | A |
| 2-(p-Bromophenyl)-4,5-dichloro-3-nitropyrrole | A | A | D | D |
| 2,3-Dichloro-4-nitro-5-(α,α,α-trifluoro-p-tolyl)pyrrole | A, F | R | D | D |
| Methiocarb | A, X | D, R | D | D |
| Check | A | A | A | A |

A = Alive
D = Dead
Z = Ooze
F = Foam Excretion
X = Extended Body
R = Reinfested

EXAMPLE 65

Arylpyrrole Activity on Fresh Water Snails

Procedure:

Gyraulis fresh water aquatic snails are used to test the activity of the arylpyrroles. The snails are collected and maintained in a tank filled with pond water which is aerated with a bottom filter. Five members of the arylpyrrole series are made up in aerated tap water (pH similar to pond water) at two dosages, 100 and 33 ppm. The compounds are initially insoluble in water at 100 ppm but with stirring and sonication, solubility is greatly improved. Three healthy snails are added to each 150 ml beaker containing 80 milliliters of treated water. A commercial standard is used as a positive check, Niclosimide. The concentrations tested are 10 and 1 ppm. An untreated check is also included.

Observations:

| Compound | PPM | % Mortality 2 Hours | % Mortality 18 Hours |
|---|---|---|---|
| 4,5-Dichloro-2-(p-chlorophenyl)-pyrrole-3-carbonitrile | 100 | 100 | 100 |
|  | 33 | O, M | 100 |
| 2,3-Dichloro-5-(p-chlorophenyl)-4-nitropyrrole | 100 | 100 | 100 |
|  | 33 | O, M | 100 |
| 4,5-Dichloro-2-(3,4-dichlorophenyl)pyrrole-3-carbonitrile | 100 | 33 | 100 |
|  | 33 | 0 | 100 |
| 2-(p-Bromophenyl)-4,5-dichloro-3-nitropyrrole | 100 | 100 | 100 |
|  | 33 | O, M | 100 |
| 2,3-Dichloro-4-nitro-5-(α,α,α-trifluoro-p-tolyl)pyrrole | 100 | 100 | 100 |
|  | 33 | O, M | 100 |
| Niclosamide | 10 | 100 | 100 |
|  | 1 | O, M | 100 |
| Check | — | 0 | 0 |

M = Moribund

The arylpyrroles produce rapid kill of this aquatic small species.

EXAMPLE 66

Arylpyrrole Activity on Pond Snails

Procedure:

Physa pond snails, obtained from Ward's Biological Supply Company, are used to assay the arylpyrroles. Five members of the arylpyrrole series are made up in aerated tap water at two dosages, 33 and 10 ppm. Three healthy snails are immersed in 10 milliliters of treated water in 20 milliliters scintillation commercial standard, Niclosamide is tested at 10 and 1 ppm and an untreated check is included.

Results:

| Compound | PPM | % Mortality at 18 Hours |
|---|---|---|
| 4,5-Dichloro-2-(p-chlorophenyl)pyrrole-3-carbonitrile | 33 | 100 |
|  | 10 | 100 |
| 2,3-Dichloro-5-(p-chlorophenyl)-4-nitropyrrole | 33 | 100 |
|  | 10 | 100 |
| 4,5-Dichloro-2-(3,4-dichlorophenyl)pyrrole-3-carbonitrile | 33 | 100 |
|  | 10 | 100 |
| 2-(p-Bromophenyl)-4,5-dichloro-3-nitropyrrole | 33 | 100 |
|  | 10 | 100 |
| 2,3-Dichloro-4-nitro-5-(α,α,α-trifluoro-p-tolyl)pyrrole | 33 | 100 |
|  | 10 | 100 |
| Niclosamide | 10 | 100 |
|  | 1 | 100 |
| Check | — | 0 |

The arylpyrroles are fast acting molluscicides on this species of fresh water snails.

EXAMPLE 67

Arylpyrrole Activity on *Helix aspersa*

Procedure:

Twenty-five *Helix aspersa*, commonly known as brown garden snails, are purchased from Ward's Biological Supply Company. Five arylpyrroles, two commercial standards and one check are then selected for testing. A 5% bait is prepared by mixing technical material (50 mg) in a bran bait (950 mg). The bait is made with 46% unprocessed bran, 6% molasses and 48% water. The treated bait is placed in a 7 ml polystyrene weight boat. The bait station is put in a 500 ml plastic deli container with one moistened dental wick. Two snails are then added to each treatment and a clear plastic lid with aeration holes is firmly placed on top of each container. The containers are examined 18 and 24 hours after the test is initiated and data obtained reported in the table below where it can be seen that the nitroarylpyrroles appear to be more effective than cyanoarylpyrroles for controlling garden variety snails *Helix aspersa*.

| Compound | % Mortality 18 Hours | % Mortality 24 Hours |
|---|---|---|
| 4,5-Dichloro-2-(p-chlorophenyl)pyrrole-3-carbonitrile | 0 | 0 |
| 2,3-Dichloro-5-(p-chlorophenyl)-4-nitropyrrole | 0* | 50* |
| 2-(p-Bromophenyl)-4,5-dichloro-3-nitropyrrole | 100 | 100 |
| 2,3-dichloro-4-nitro-5-(α,α,α-trifluoro-p-tolyl)pyrrole | 100 | 100 |
| Methiocarb | 0* | 0* |
| Metaldehyde | 100 | 100 |
| Check | 0 | 0 |

*Moribund

What is claimed is:

1. A method for controlling mollusks comprising externally contacting said mollusks or internally administering to said mollusks a molluscicidally effective amount of an arylpyrrole compound having the structure:

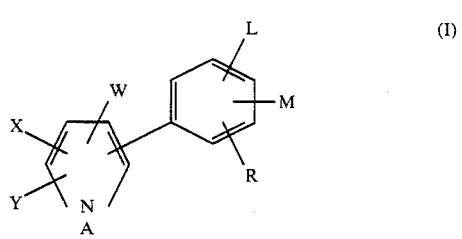

wherein X is F, Cl, Br, I, or CF$_3$; Y is F, Cl, Br, I, CF$_3$ or CN; W is CN or NO$_2$; A is H; C$_1$–C$_4$ alkyl optionally substituted with from one to three halogen atoms, one hydroxy, one C$_1$–C$_4$ alkoxy, one C$_1$–C$_4$ alkylthio, one phenyl optionally substituted with C$_1$–C$_3$ alkyl, C$_1$–C$_3$ alkoxy or from one to three halogen atoms, one phenoxy optionally substituted with one to three halogen atoms or one benzyloxy optionally substituted with one halogen substituent; $C_1$-$C_4$ carbalkoxymethyl; $C_3$-$C_4$ alkenyl optionally substituted with from one to three halogen atoms; cyano; $C_3$-$C_4$ alkynyl optionally substituted with one halogen atom; di-($C_1$-$C_4$ alkyl) aminocarbonyl; or $C_4$-$C_6$ cycloalkylaminocarbonyl; L is H, F, Cl or Br; and M and R are each independently H, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, cyano, F, Cl, Br, I, nitro, $CF_3$, $R_1CF_2Z$, $R_2CO$ or $NR_3R_4$, and when M and R are on adjacent positions and taken with the carbon atoms to which they are attached they may form a ring i.n which MR represents the structure:

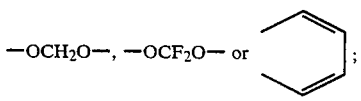

Z is S(O)n or O; $R_1$ is H, F, $CHF_2$, $CHFCl$, or $CF_3$; $R_2$ is $C_1$-$C_3$ alkyl, $C_1$-$C_3$ alkoxy, or $NR_3R_4$; $R_3$ is H or $C_1$-$C_3$ alkyl; $R_4$ is H, $C_1$-$C_3$ alkyl, or $R_5CO$; $R_5$ is H or $C_1$-$C_3$ alkyl; and n is an integer of 0, 1 or 2.

2. A method according to claim 1 wherein the arylpyrrole has the structure of formula II:

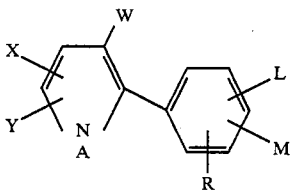

and wherein A, L, M, R, W, X and Y are as described in the above-said claim 1.

3. A method according to claim 1 wherein said mollusks are aquatic, semi-aquatic or terrestrial gastropods and controlled by applying to the locus of said gastropods a molluscicidally effective amount of the arylpyrrole of said claim 1 in the form of a wettable powder, flowable, microemulsion, dust, dust concentrate or bait formulation.

4. A method according to claim 3 wherein the terrestrial gastropods are slugs or snails.

5. A method according to claim 4 wherein the slugs are controlled by administering thereto a bait formulation containing an edible nutritive substance, an edible carbohydrate source, water and an effective amount of the arylpyrrole.

6. A method according to claim 5 wherein the arylpyrrole is as described above and A is hydrogen, $C_1$-$C_4$ alkoxymethyl or benzyl optionally substituted with one or two $C_1$-$C_4$ alkyl, $C_1$-$C_4$ alkoxy or halogen groups; W is CN or $NO_2$; X and Y are each F, Cl or Br; L is H, F, Cl or Br; M is H, F, Cl, Br, $CF_3$, $CH_3$, $OCH_3$, $OCF_3$, $OCH_2CF_3$, $SO_2CH_3$, CN, $OCF_2CHF_2$, $OCHF_2$, $SCH_3$ or $NO_2$; and R is hydrogen.

7. A method according to claim 5 wherein the arylpyrrole compound is 2,3-dichloro-4-nitro-5-phenylpyrrole; 2,3-dichloro-5-(p-chlorophenyl)-4-nitropyrrole; 2,3-dibromo-5-(p-chlorophenyl)-4-nitropyrrole; 2-(p-bromophenyl)-4,5-dichloro-3-nitropyrrole; 2,3-dichloro-4-nitro-5-(α,α,α-trifluoro-p-tolyl)pyrrole; 4,5-dichloro-2-(3,4-dichlorophenyl)pyrrole-3-carbonitrile; 1-benzyl-4,5-dichloro-2-(3,4-dichlorophenyl)pyrrole-3-carbonitrile; or 4,5-dichloro-2-(p-chlorophenyl)pyrrole-3-carbonitrile.

8. A molluscicidal bait formulation comprising: an edible nutritive substance, a carbohydrate source, water and a molluscicidally effective amount of a compound having the structure:

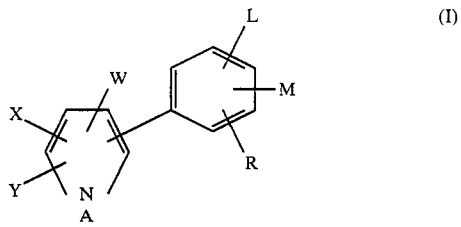

wherein X is F, Cl, Br, I, or $CF_3$; Y is F, Cl, Br, I, $CF_3$ or CN; W is CN or $NO_2$; A is H; $C_1$-$C_4$ alkyl optionally substituted with from one to three halogen atoms, one hydroxy, one $C_1$-$C_4$ alkoxy, one $C_1$-$C_4$ alkylthio, one phenyl optionally substituted with $C_1$-$C_3$ alkyl, $C_1$-$C_3$ alkoxy or from one to three halogen atoms, one phenoxy optionally substituted with one to three halogen atoms or one benzyloxy optionally substituted with one halogen substituent; $C_1$-$C_4$ carbalkoxymethyl; $C_3$-$C_4$ alkenyl optionally substituted with from one to three halogen atoms; cyano; $C_3$-$C_4$ alkynyl optionally substituted with one halogen atom; di-($C_1$-$C_4$ alkyl) aminocarbonyl; or $C_4$-$C_6$ cycloalkylaminocarbonyl; L is H, F, Cl or Br; and M and R are each independently H, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, cyano, F, Cl, Br, I, nitro, $CF_3$, $R_1CF_2Z$, $R_2CO$ or $NR_3R_4$, and when M and R are on adjacent positions and taken with the carbon atoms to which they are attached they may form a ring in which MR represents the structure:

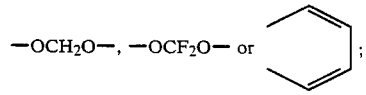

Z is S(O)n or O; $R_1$ is H, F, $CHF_2$, $CHFCl$, or $CF_3$; $R_2$ is $C_1$-$C_3$ alkyl, $C_1$-$C_3$ alkoxy, or $NR_3R_4$; $R_3$ is H or $C_1$-$C_3$ alkyl; $R_4$ is H, $C_1$-$C_3$ alkyl, or $R_5CO$; $R_5$ is H or $C_1$-$C_3$ alkyl; and n is an integer of 0, 1 or 2.

9. A molluscicidal bait formulation according to claim 8 where said formulation comprises about 3% to 20% by weight of said arylpyrrole; about 40% to 50% by weight of said edible nutritive substance; about 5% to 10% by weight of carbohydrate and q.s. to 100% with water.

10. A molluscicidal bait formulation according to claim 8 wherein the arylpyrrole is: 2,3-dichloro-4-nitro-5-phenylpyrrole; 2,3-dichloro-5-(p-chlorophenyl)-4-nitropyrrole; 2,3-dibromo-5-(p-chlorophenyl)-4-nitropyrrole; 2-(p-bromophenyl)-4,5-dichloro-3-nitropyrrole; 2,3-dichloro-4-nitro-5-(α,α,α-trifluoro-p-tolyl)pyrrole; 4,5-dichloro-2-(3,4-dichlorophenyl)pyrrole-3-carbonitrile; 1-benzyl-4,5-dichloro-2-(3,4-dichlorophenyl)pyrrole-3-carbonitrile; or 4,5-dichloro-2-(p-chlorophenyl)pyrrole-3-carbonitrile.

11. A method for protecting plants from attack by terrestrial gastropods by applying to the soil in which said plants are growing, a molluscicidally effective amount of the bait formulation of claim 8.

12. A method for protecting plants from attack by terrestrial gastropods by applying to the foliage of said plants a molluscicidally effective amount of the bait formulation of claim 8 as a dust, dust concentrate or liquid spray.

13. A method according to claim 12 wherein said bait formulation is applied as a dust, dust concentrate or liquid spray in sufficient amount to provide about 0.125 kg/ha to 4.0 kg/ha of the arylpyrrole to the locus of treatment.

14. A method according to claim 13 wherein said arylpyrrole is: 2,3-dichloro-4-nitro-5-phenylpyrrole; 2,3-dichloro-5-(p-chlorophenyl)-4-nitropyrrole; 2,3-dibromo-5-(p-chlorophenyl)-4-nitropyrrole; 2-(p-bromophenyl)-4,5-dichloro-3-nitropyrrole; 2,3-dichloro-4-nitro-5-($\alpha,\alpha,\alpha$-trifluoro-p-tolyl)pyrrole; 4,5-dichloro-2-(3,4-dichlorophenyl)pyrrole-3-carbonitrile; 1-benzyl-4,5-dichloro-2-(3,4-dichlorophenyl)pyrrole-3-carbonitrile; or 4,5-dichloro-2-(p-chlorophenyl)pyrrole-3-carbonitrile.

* * * * *